(12) United States Patent
Douniama et al.

(10) Patent No.: US 9,119,536 B2
(45) Date of Patent: Sep. 1, 2015

(54) PRESSURE GAUGE, BLOOD PRESSURE GAUGE, METHOD OF DETERMINING PRESSURE VALUES, METHOD OF CALIBRATING A PRESSURE GAUGE, AND COMPUTER PROGRAM

(75) Inventors: Christian Douniama, Erlangen (DE); Andreas Tobola, Hemhofen (DE); Holger Wentzlaff, Nuremberg (DE); Michaela Benz, Erlangen (DE); Thomas Norgall, Eckental (DE); Robert Couronne, Erlangen (DE); Christian Weigand, Fuerth (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 860 days.

(21) Appl. No.: 12/812,280

(22) PCT Filed: Dec. 30, 2008

(86) PCT No.: PCT/EP2008/011153
§ 371 (c)(1),
(2), (4) Date: Nov. 22, 2010

(87) PCT Pub. No.: WO2009/086921
PCT Pub. Date: Jul. 16, 2009

(65) Prior Publication Data
US 2012/0065525 A1     Mar. 15, 2012

(30) Foreign Application Priority Data

Jan. 11, 2008 (DE) .......................... 10 2008 003 978

(51) Int. Cl.
*A61B 5/02* (2006.01)
*A61B 5/021* (2006.01)
(Continued)

(52) U.S. Cl.
CPC .......... *A61B 5/02125* (2013.01); *A61B 5/0285* (2013.01); *A61B 5/02116* (2013.01); *A61B 5/0535* (2013.01)

(58) Field of Classification Search
USPC ......................................................... 600/485
See application file for complete search history.

(56) References Cited

U.S. PATENT DOCUMENTS 4,245,648 A    1/1981   Trimmer et al.
6,331,162 B1  12/2001   Mitchell
(Continued)

FOREIGN PATENT DOCUMENTS

DE    100 61 189 A1    6/2002
EP    1 157 658 A1    11/2001
(Continued)

OTHER PUBLICATIONS

Official Communication issued in International Patent Application No. PCT/EP2008/011153, mailed on Apr. 6, 2009.

*Primary Examiner* — Michael Kahelin
*Assistant Examiner* — Mitchell E Alter
(74) *Attorney, Agent, or Firm* — Keating & Bennett, LLP

(57) ABSTRACT

A pressure gauge for determining at least one pressure value describing a pressure of a fluid flowing in a pulsating manner in a phase of the pulsating flow, includes a pulse wave characterizer. The pulse wave characterizer is configured to obtain transmit time information of a pulse wave, and amplitude information of the pulse wave. The pressure gauge additionally includes a pressure value determiner configured to obtain a first pressure value describing a pressure of the fluid in a first phase, on the basis of the transmit time information and while using a mapping. The pressure value determiner is further configured to obtain a second pressure value describing a pressure of the fluid in a second phase, on the basis of the first pressure value and the amplitude information while using a mapping.

33 Claims, 11 Drawing Sheets

(51) Int. Cl.
 *A61B 5/0285* (2006.01)
 *A61B 5/053* (2006.01)

(56) References Cited

U.S. PATENT DOCUMENTS

| | | |
|---|---|---|
| 6,648,828 B2 | 11/2003 | Friedman et al. |
| 6,736,789 B1 | 5/2004 | Spickermann |
| 7,029,447 B2 | 4/2006 | Rantala |
| 8,147,416 B2 * | 4/2012 | Fayram et al. ............... 600/486 |
| 2004/0162493 A1 | 8/2004 | Mills |
| 2005/0261593 A1 | 11/2005 | Zhang et al. |
| 2008/0039731 A1 * | 2/2008 | McCombie et al. .......... 600/485 |

FOREIGN PATENT DOCUMENTS

| | | |
|---|---|---|
| EP | 2 030 564 A2 | 3/2009 |
| GB | 2 394 178 A | 4/2004 |
| KR | 10-2006-0069032 A | 6/2006 |
| KR | 10-0697211 B1 | 3/2007 |

\* cited by examiner

PRESSURE GAUGE, BLOOD PRESSURE GAUGE, METHOD OF DETERMINING PRESSURE VALUES, METHOD OF CALIBRATING A PRESSURE GAUGE, AND COMPUTER PROGRAM Embodiments in accordance with the invention relate to a pressure gauge, a blood pressure gauge, a method of determining pressure values, a method of calibrating a pressure gauge, and a computer program.

Some embodiments in accordance with the invention relate to methods of non-invasive, continuous blood pressure measurement without a cuff by using two plethysmographs on the forearm on the basis of a pulse wave transmit time and a pulse wave amplitude.

BACKGROUND OF THE INVENTION

In many situations it is desirable to measure a blood pressure of a human being or an animal. Generally, measurement of a pressure existing, for example, in an elastic fluid conductor (for example a tube, a thin-walled pipe or a blood vessel) may be used in order to monitor, for example, the function of a pump or other process parameters.

The "blood pressure", which is a vital parameter, is e.g. a transmural pressure at arterial vascular walls which results from a difference between an internal pressure and an external pressure of the vessel (or blood vessel). By a contraction of the heart and a simultaneous expulsion of blood from a left ventricle into the aorta, a pressure forms within an aortic arch (for example within the vessel) due to the incompressibility of the blood, said pressure propagating as a pressure wave (also known as a pulse wave) from the aorta to a periphery (of a human being or an animal) and resulting in a short-time change in the volume (or local change in the volume or change in the cross section) of a section of the vessel observed. In this context, one distinguishes, e.g., between a systolic and a diastolic blood pressure value, and defines them accordingly as a maximum (systolic) and a minimum (diastolic) vessel pressure in the course of a cardiac cycle.

Various methods of blood pressure measurement are already known. For example, U.S. Pat. No. 6,736,789 B1 describes a method and a device for blood treatment using a device for continuously monitoring the blood treatment performed outside the body. A blood pressure of a patient, or a quantity correlated with the blood pressure, is measured and compared with a predetermined limiting value. If the blood pressure measured, or its relative change, falls below the predetermined limiting value, a signal is created in order to interrupt the sequence of treatments. Continuous non-invasive measurement of the blood pressure is based on a determination of the propagation velocity or transmit time of the pulse waves created by the heart contractions of the patient and by the propagation through the arterial system. To determine the pulse wave velocity or transmit time, the blood treatment machine comprises an electrocardiograph as well as means for detecting the pulse waves at a location remote from the person's heart.

GB 2394178 A describes a method of calibrating a blood pressure monitoring apparatus. A blood pressure measuring apparatus is calibrated by measuring the blood pressure of a living organism while using a manometer. In addition, a reference transmit time of a blood pulse wave is measured which travels from the heart along a blood vessel to a region that is remote from the heart. An arrival of the blood pulse wave at the fingertip is detected by using a plethysmograph. A first measurement of a blood pressure and of a transmit time is used for creating a first calibration data point. That region of the body that is remote from the heart is then raised and lowered down starting from a position that is at the same level as the heart. A transmit time is measured for the raised and lowered-down position. Subsequently, a blood pressure difference is calculated between a state wherein the region is raised or lowered down. A transmit time difference between the raised and the lowered-down position is calculated, and a second data point is created from the calculated blood pressure difference and transmit time difference.

U.S. Pat. No. 7,029,447 B2 describes a device and a system for non-invasive measurement of a blood pressure of a patient. The method comprises the following steps: determining a mechanical heartbeat starting time from an impedance cardiography signal, detecting a heartbeat pulse arrival time at a peripheral location of the patient, computing a pulse wave transmit time from the heart to the peripheral location while using the mechanical starting time of the heartbeat and the heartbeat pulse arrival time, as well as calculating an estimated value of a blood pressure of the patient from the pulse wave transmit time.

U.S. Pat. No. 6,648,828 B2 describes a continuous, non-invasive method of measuring blood pressure while using impedance plethysmography. A blood pressure is measured while utilizing a pulse transmit time that may be taken by the blood volume pulse to propagate between two locations in an animal. Impedance plethysmography is used for detecting when the blood volume pulse occurs at a location. The plethysmograph may detect a thorax impedance to determine when the aorta heart valve opens, or it may detect an impedance at a location of an extremity of the animal. The occurrence of the blood volume pulse at a different location may be determined by means of impedance plethysmography or another technology, such as pulse oxymetry. Calculation of a heartbeat volume may be used for compensating for any deviation of the blood pressure that may be due to effects based on an expansibility of the blood vessel. A blood pressure monitor may periodically provide a reference blood pressure measurement that is used for calibrating the derivation of the blood pressure on the basis of the pulse transmit time.

U.S. Pat. No. 6,331,162 B1 describes a device for measuring a pulse wave velocity. The device comprises first and second plethysmograph sensors connected to a computer. The sensors are positioned on the back of a patient so as to record pulse waveform information at two locations along the thoracic aorta. In addition, an electrocardiogram of the patient is recorded. As soon as the pulse waveforms and the electrocardiogram waveform have been recorded, data that is noisy or comprises artefacts is excluded, and the pulse waveforms are determined utilizing the electrocardiogram data points. Subsequently, the signal-averaged pulse waveforms are analyzed to determine a foot of each waveform and to determine a foot-to-foot transmit time between the two sensors. A pulse wave velocity is subsequently determined by dividing the distance between the sensors by the foot-to-foot transmit time.

Further aspects with regard to blood pressure measurement are also described in KR 000100697211 BA and in KR 102006069032 AA.

SUMMARY

According to an embodiment, a pressure gauge for determining at least one pressure value describing a pressure of a fluid flowing in a pulsating manner in a phase of the pulsating flow may have: a pulse wave characterizer configured to acquire transmit time information describing a transmit time of a pulse wave between a first location and a second location, and amplitude information describing a change in a measurement signal, which is based on the pulse wave, between two phases of the pulse wave; and a pressure value determiner configured to acquire a first pressure value describing a pressure of the fluid in a first phase of the pulsating flow on the basis of the transmit time information and while using a first mapping which maps the transmit time of the pulse wave to the first pressure value, and to acquire a second pressure value describing a pressure of the fluid in a second phase of the pulsating flow on the basis of the first pressure value and the amplitude information while using a second mapping, the second mapping describing a relationship, which depends on the first pressure value, between the first pressure value, the second pressure value and the amplitude information.

According to another embodiment, a method of determining, while using a pressure gauge, pressure values which describe a pressure of a fluid that is flowing in a pulsating manner in at least two phases of the pulsating flow may have the steps of: acquiring transmit time information describing a transmit time of a pulse wave between a first location and a second location; acquiring amplitude information describing a change in a measurement signal, based on a pulse wave, between two phases of the pulse wave; determining a first pressure value, which describes a pressure of the fluid in a first phase of the pulsating fluid, on the basis of the transmit time information and while using a first mapping, which maps a transmit time of the pulse wave to the first pressure value; and determining a second pressure value, which describes a pressure of the fluid in a second phase of the pulsating flow, on the basis of the first pressure value and of the amplitude information, while using a second mapping, which describes a relationship—which is dependent on the first pressure value— between the first pressure value, the second pressure value and the amplitude information.

According to another embodiment, a method of calibrating a pressure gauge configured to determine, while using a first mapping and a second mapping, at least one pressure value which describes a pressure of a fluid flowing in a pulsating manner in a phase of the pulsating flow may have the steps of: determining a plurality of pieces of reference transmit time information describing transmit times of pulse waves between a first location and a second location for a plurality of pressure values, and a plurality of associated reference pressure values; determining the first mapping, which describes a relationship between transmit times of the pulse waves and associated pressure values, while using the reference transmit time information and the reference pressure values; and determining the second mapping, which describes a relationship, that is dependent on a first pressure value, between the first pressure value, a second pressure value and amplitude information, a qualitative course of the second mapping being specified on the basis of the first mapping.

Another embodiment may have a computer program for performing a method of determining, while using a pressure gauge, pressure values which describe a pressure of a fluid that is flowing in a pulsating manner in at least two phases of the pulsating flow, which method may have the steps of: acquiring transmit time information describing a transmit time of a pulse wave between a first location and a second location; acquiring amplitude information describing a change in a measurement signal, based on a pulse wave, between two phases of the pulse wave; determining a first pressure value, which describes a pressure of the fluid in a first phase of the pulsating fluid, on the basis of the transmit time information and while using a first mapping, which maps a transmit time of the pulse wave to the first pressure value; and determining a second pressure value, which describes a pressure of the fluid in a second phase of the pulsating flow, on the basis of the first pressure value and of the amplitude information, while using a second mapping, which describes a relationship—which is dependent on the first pressure value— between the first pressure value, the second pressure value and the amplitude information, when the method is performed on a computer.

Another embodiment may have a computer program for performing a method of calibrating a pressure gauge configured to determine, while using a first mapping and a second mapping, at least one pressure value which describes a pressure of a fluid flowing in a pulsating manner in a phase of the pulsating flow, which method may have the steps of: determining a plurality of pieces of reference transmit time information describing transmit times of pulse waves between a first location and a second location for a plurality of pressure values, and a plurality of associated reference pressure values; determining the first mapping, which describes a relationship between transmit times of the pulse waves and associated pressure values, while using the reference transmit time information and the reference pressure values; and determining the second mapping, which describes a relationship, that is dependent on a first pressure value, between the first pressure value, a second pressure value and amplitude information, a qualitative course of the second mapping being specified on the basis of the first mapping, when the method is performed on a computer.

Some embodiments in accordance with the invention are based on the finding that a particularly reliable determination of a pressure value may be obtained on the basis of a measurement signal by initially evaluating transmit time information describing a transmit time of a pulse wave between a first location and a second location, so as to obtain a first blood pressure value, and by subsequently determining, on the basis of the amplitude information, a second pressure value while using a second mapping which describes a relationship, which is dependent on the first blood pressure value, between amplitude information and an amplitude of a pulse wave described by the measurement signal.

It has been found, specifically, that a relationship between the amplitude information describing, e.g., the amplitude of the measurement signal, and the amplitude of a pulse wave described by the measurement signal is dependent on the applied pressure on account of the properties of an elastic fluid conductor. Thus, in pressure measurement, for example, one takes into account, or exploits, the fact that with an elastic fluid conductor that is already heavily expanded (e.g. a blood vessel), a certain change in volume corresponds to a comparatively large change in pressure, whereas with a fluid conductor that is less heavily expanded, the same change in volume corresponds to a comparatively smaller change in pressure.

Thus, for example, a specific amplitude of a measurement signal describing, e.g., a (local) volume of a fluid conductor or a cross-sectional area of a fluid conductor (for example as a function of time) may be mapped, in dependence on the first blood pressure value, to an amplitude of a pulse wave described by the measurement signal (i.e., for example, to a difference between two pressure values, for example, in the case of blood pressure measurement, to a difference between a systolic and a diastolic blood pressure value).

By indirectly determining the second pressure value, the amplitude information describing the amplitude of the measurement signal may thus be evaluated, in which context it is to be stated that an amplitude of the measurement signal may typically be determined in a very efficient and precise manner.

To achieve improved accuracy, however, the first pressure value is also taken into account for the second mapping, which describes a relationship between the amplitude of the measurement signal and an amplitude of a pulse wave (or a pressure difference).

The approach mentioned may enable, for example, that the transmit time is determined only for such a first pressure value for which a transmit time measurement is possible in a particularly reliable or precise manner. The amplitude of the measurement signal may then be used for obtaining, on the basis of the first pressure value, the second pressure value—which might be determined, for example, only with less precision by means of a transmit time measurement. With some embodiments, this may result in a particularly precise measurement, since the amplitude of a measurement signal is in many cases a parameter of a measurement signal that may be determined in a particularly precise manner.

Therefore, it is not required, in accordance with some embodiments, to directly determine the second pressure value (e.g. a minimum or smaller pressure value of a pulse wave) by means of a transmit time measurement, which under certain circumstances may be difficult and error-prone. Rather, for example, the lower, or smaller, pressure value (e.g. a diastolic pressure value) may be indirectly determined on the basis of the determination of an upper, or larger, pressure value (e.g. a systolic pressure value) and on the basis of an amplitude of a measurement signal. The amplitude of the measurement signal may be mapped—as a function of the upper, or larger, pressure value determined (systolic pressure value)—to the lower, or smaller, pressure value, for which purpose the second mapping, which is dependent on the first pressure value, may be used.

In summary, it may therefore be stated that in accordance with some embodiments, an indirect concept for pressure determination or for determining a pressure value is provided which leads to a particularly high precision when determining some pressure values (e.g. when determining a lower, or smaller, pressure value, or a diastolic pressure value).

Some embodiments in accordance with the invention relate to a blood pressure gauge, wherein the concept described herein is employed for measuring a blood pressure value, e.g. a systolic blood pressure value or a diastolic blood pressure value.

In some embodiments, the inventive concept may also be efficiently used for determining two different blood pressure values, for example both a systolic blood pressure value and a diastolic blood pressure value.

Some embodiments in accordance with the invention relate to a method of measuring pressure values.

Further embodiments of the invention relate to a method of calibrating a pressure gauge.

Some embodiments in accordance with the invention are based on the core idea that for calibrating a pressure gauge, determination of two mappings leads to particularly good results. A first mapping, which is created or determined in the calibration, or in the method of calibrating a pressure gauge, or for which parameters are determined during calibration, describes a relationship between transmit times of the pulse waves and associated pressure values. Subsequently, a second mapping is created on the basis of the first mapping. By creating the second mapping on the basis of the first mapping, one may achieve that a qualitative course of the second mapping describes a pressure-dependent connection between local volume values or local change-in-volume values of the fluid conductor within which the pulse wave is propagating, and associated pressure values or pressure differences. Thus, the determination of the second mapping is simplified by the fact that the second mapping is based on the first mapping, since there is a close relationship between a mapping which describes a relationship between transmit times of the pulse waves and associated pressure values, and a mapping which describes a relationship between local volume values and associated pressure values. In that the second mapping is obtained on the basis of the first mapping, at least a qualitative course of the second mapping may therefore be specified without a large amount of metrological expenditure. Rather, in some embodiments, the second mapping or its qualitative course arises directly from the first mapping, without using any further measurement values.

A scaling quantity of the second mapping may be specified in a very simple manner on the basis of two reference pressure values and at least two corresponding signal values of a measurement signal.

Therefore, it is to be stated that both the first mapping and the second mapping may be determined in a particularly efficient manner when calibrating a pressure gauge. For specifying the first mapping and the second mapping, only a very small number of measurements, or measurement values, may be used.

Against this background, some embodiments in accordance with the invention provide a particularly efficient calibration, in which context it may be stated that the mappings or mapping specifications obtained by the calibration may be exploited, in turn, for determining particularly precise results, as was already set forth above.

The above and other elements, features, steps, characteristics and advantages of the present invention will become more apparent from the following detailed description of the preferred embodiments with reference to the attached drawings.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
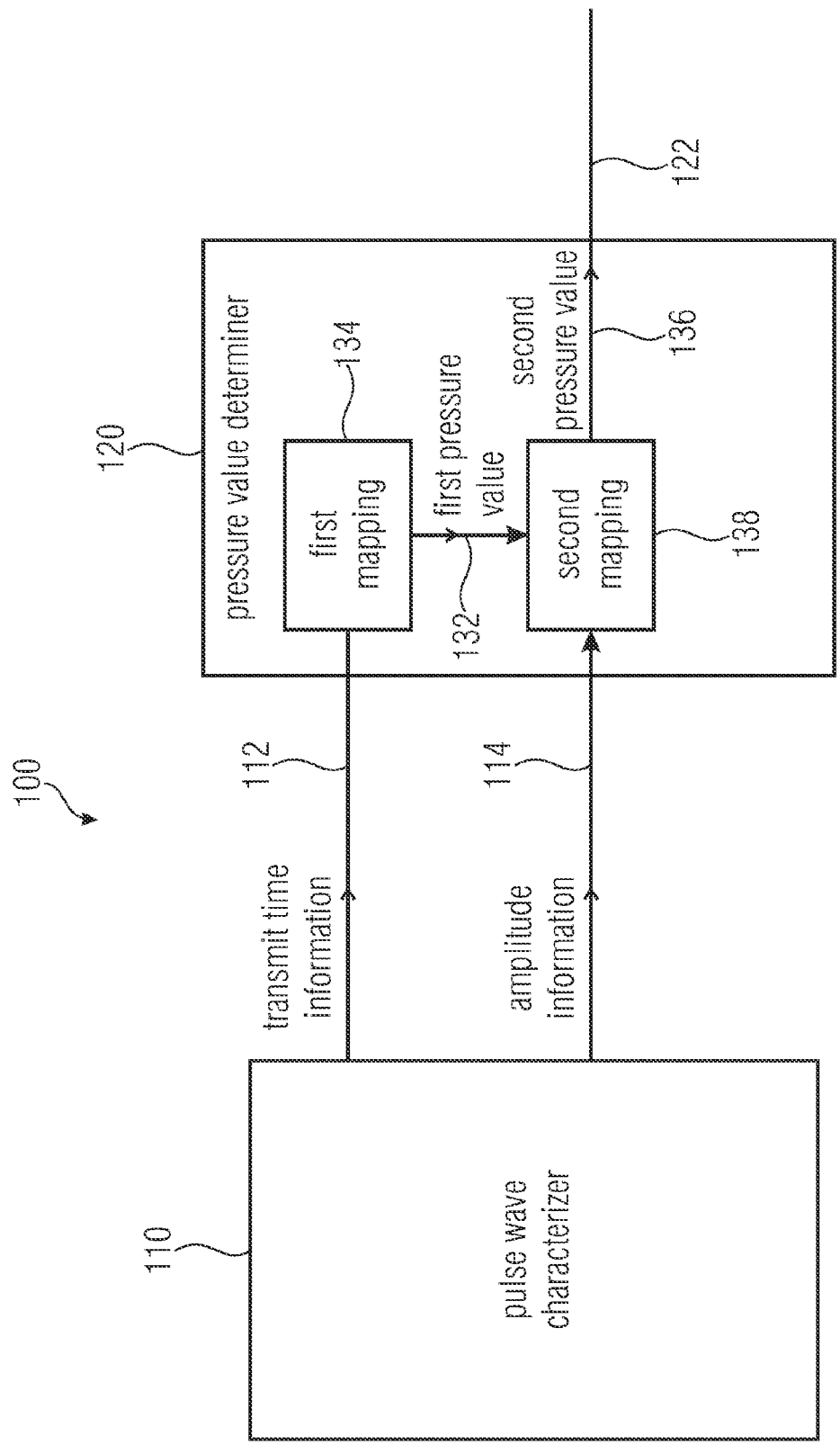
FIG. 1 shows a block diagram of a pressure gauge in accordance with an embodiment of the invention.

FIG. 1 shows a block diagram of a pressure gauge in accordance with an embodiment of the invention. The pressure gauge of FIG. 1 is designated by 100 in its entirety. The pressure gauge 100 comprises a pulse wave characterizer 110. The pulse wave characterizer 110 is configured to provide transmit time information 112 describing a transmit time of a pulse wave between a first location and a second location. In addition, the pulse wave characterizer 110 is configured to provide amplitude information 114 describing a change in a measurement signal, which is based on the pulse wave, between two phases of the pulse wave. The pressure gauge further comprises a pressure value determiner 120. The pressure value determiner 120 is configured to receive the transmit time information 112 and the amplitude information 114 so as to provide, on the basis thereof, at least one pressure value 122 (here referred to as a "second pressure value").

For example, the pressure value determiner 120 is configured to obtain a first pressure value 132, which describes a pressure of a fluid in a first phase of a pulsating flow, on the basis of the transmit time information 112 and while using a first mapping 134, which maps the transmit time of a pulse wave to the first pressure value.

The pressure value determiner 120 is further configured to determine, on the basis of the first pressure value 132 and the amplitude information 114, a second pressure value 136, which corresponds, for example, to the pressure value 122 provided as output information by the pressure value determiner 120, and which describes, for example, a pressure of the fluid in a second phase of the pulsating flow. To achieve this, one uses, e.g., a second mapping 138 describing a relationship, which is dependent on the first pressure value 132, between the first pressure value, the second pressure value 136 and the amplitude information 114.

With regard to the functionality of the pressure gauge 100, it is therefore to be stated that the second pressure value 136 is generated on the basis of on the transmit time information 112 and the amplitude information 114 in a multi-stage system or method while using several mappings 134, 138. The transmit time information 112 is initially evaluated within the context of the first mapping 134 in order to determine the first pressure value 132. Subsequently, the second pressure value 136 is determined, starting from the first pressure value, while using the second mapping 138 and while taking into account the amplitude information 114. The second mapping 138 may describe, for example in a direct or indirect manner, to which extent the second pressure value 136 differs from the first pressure value 132. In this context, for example, the second mapping may describe that a difference between the first pressure value 132 and the second pressure value 136 is dependent not only on the amplitude information 114, but also on the first pressure value 132. Thus, for example, the expansion of an elastic fluid conductor (e.g. a blood vessel)—said expansion being non-linearly variable with the pressure—may be taken into account for calculating the second pressure value 136, it being possible, for example, for the first pressure value 132 to provide information about the extent to which the elastic fluid conductor is expanded when it is in a state in which the transmit time information 112 is obtained.

Thus, the pressure gauge 100 may provide, for example, particular precise and reliable information about the second pressure value 136, in which context both the transmit time information and the amplitude information are exploited.

Further details will be described below.

Figure 2A:
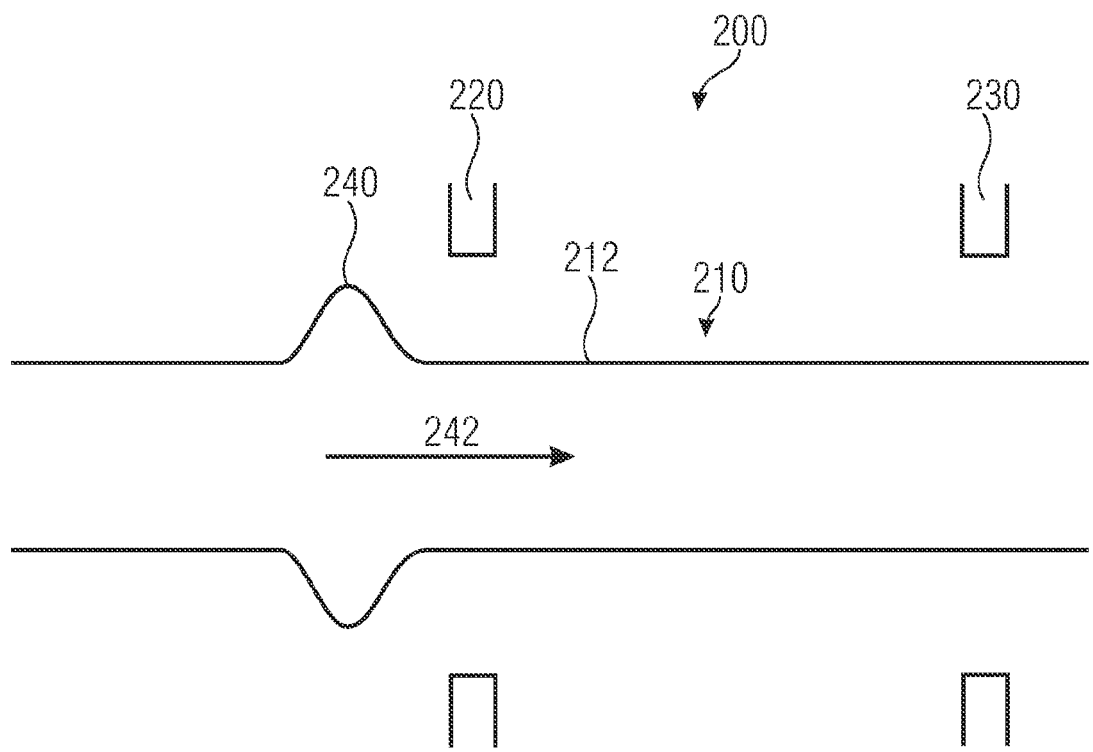
FIG. 2a shows a schematic representation of a pulse wave within an elastic fluid conductor at a first point in time.
Figure 2B:
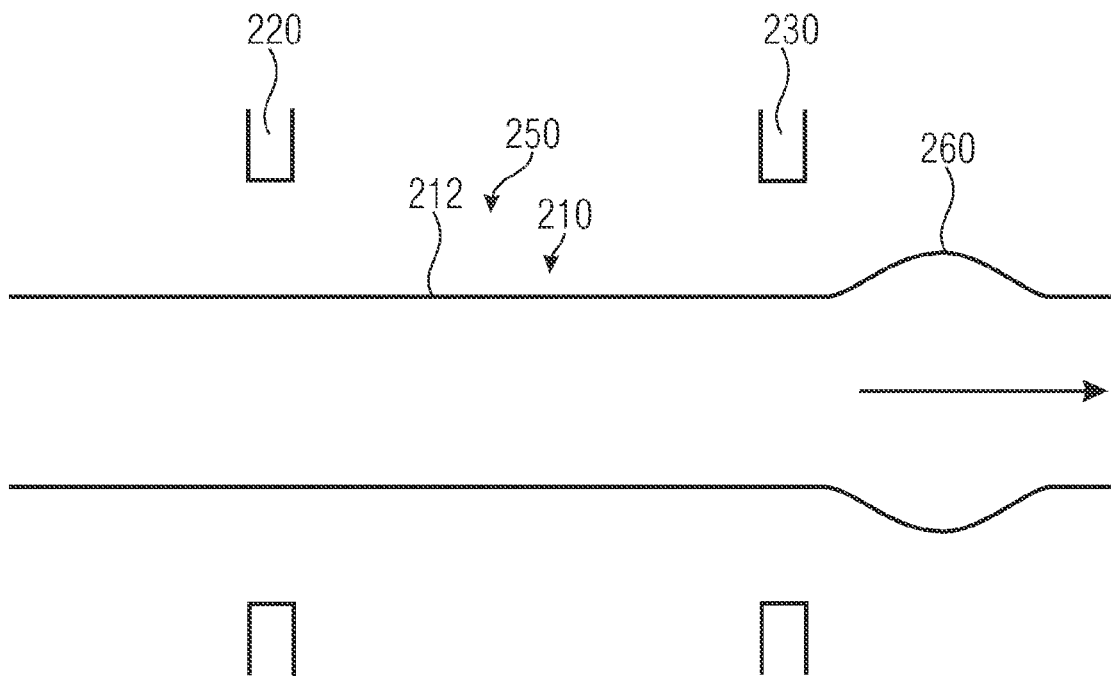
FIG. 2b shows a schematic representation of the pulse wave within the elastic fluid conductor at a second point in time.

To further understanding, FIGS. 2a and 2b show schematic representations of an elastic fluid conductor within which a pulse wave propagates over time.

The schematic representation of FIG. 2a is designated by 200 in its entirety. The schematic representation of FIG. 2b is designated by 250 in its entirety. Identical reference numerals are used in FIGS. 2a and 2b for designating identical means or features.

The schematic representation 200 shows a cross section through a fluid conductor 210. An elastic wall of the fluid conductor is designated by 212. A propagation of a pulse wave within the fluid conductor 210 may be recognized, for example, in that the wall 212 of the fluid conductor 210 is arched outward at a site where the pulse wave is being located.

The schematic representation 200 of FIG. 2a schematically shows, for example, a first sensor 220 and a second sensor 230. The first sensor is adapted, for example, to recognize a local enlargement of (or change in) a cross section of the fluid conductor 210 at a first location. The second sensor 230 is adapted, for example, to recognize a local enlargement of (or change in) a cross section of the fluid conductor 210 at a second location.

Thus, the first sensor 220 provides, for example, a first measurement signal describing, e.g., a function of a local diameter, of a local cross-sectional area or of a local volume (for example at a predefined first location or for a first section) of the elastic fluid conductor 210 at a first location, or for a first section of the fluid conductor. Accordingly, the second sensor 230 provides, for example, a second measurement signal describing a local diameter, a local cross-sectional area or a local volume (for example of a section) of the fluid conductor 210 (for example at a predefined second location or for a second section).

FIGS. 2a and 2b further show a pulse wave. For example, the schematic representation 200 of FIG. 2a depicts a cross-sectional enlargement, caused by the pulse wave, of the elastic fluid conductor 210. The pulse wave propagates from the left to the right, for example, as is represented by an arrow 242. Thus, the pulse wave propagates, in the direction designated by the arrow 242, between a first point in time at which the state shown in the schematic representation 200 is present, and a second point in time at which the state shown in the schematic representation 250 is present. Thus, a local cross-sectional enlargement 260, which may be seen in the schematic representation 250, results at the second point in time. With the propagation of the pulse wave, the local enlargement of the cross-sectional area of the elastic fluid conductor 210 thus moves past both sensors 220, 230. The corresponding movement of the local diameter enlargement or local cross-sectional area enlargement or local volume enlargement is reflected in corresponding pulses in the first measurement signal and in the second measurement signal, as will be described below.

A shape of the pulse wave or of the diameter enlargement or cross-sectional area enlargement caused by the pulse wave may change over the course of the propagation of the pulse wave. For example, a spatially closely concentrated pulse wave may become a spatially extensive pulse wave over the course of the propagation, as may be seen from FIGS. 2a and 2b (cf. local cross-sectional enlargements 240 and 260). Accordingly, the measurement signal provided by the first sensor 220 may, for example, have a short and intense pulse-shaped course, whereas the measurement signal provided by the second sensor 230 comprises a longer, but less intense course.

It shall be noted that the propagation of a pulse wave that has been explained in terms of FIGS. 2a and 2b may equally occur within a blood vessel or in any other elastic fluid conductor. In this regard, there are no major differences also with regard to the measurement signals yielded during blood pressure measurement as compared to the measurement signals yielded when a pressure in a technical installation or in a technical system is reported. Thus, the concept described may be employed both for blood pressure measurement and for pressure measurement in technical installations or systems.

Figure 3:
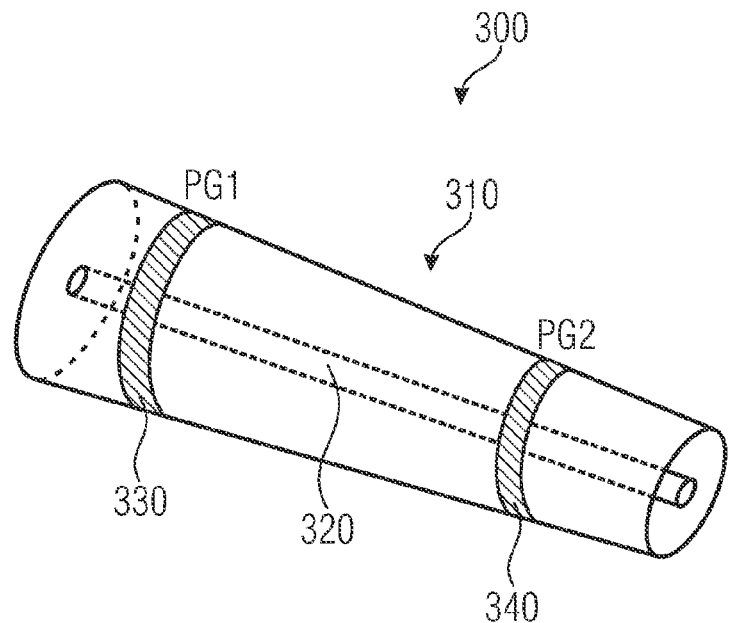
FIG. 3 shows a schematic representation of an arm having two plethysmographs arranged thereon.

FIG. 3 shows a schematic representation of a forearm 310 and of a course of an arteria ulnaris and an arteria radialis. The arteries are indicated, for example, by a dashed line 320, no explicit difference being made here between the arteria ulnaris and the arteria radialis.

This schematic representation of FIG. 3 is designated by 300 in its entirety and further schematically shows a first plethysmograph 330 arranged at a first location or at a first position on the forearm 310. For example, the first plethysmograph 330 is configured to detect local changes in a diameter, in a cross-sectional area or in a (local) volume of the arteria ulnaris and/or the arteria radialis, and to describe same by means of a first measurement signal. The schematic representation 300 further shows a second plethysmograph 340 arranged at a second position or location of the forearm 310. For example, the second plethysmograph 340 is configured to detect local changes in a diameter, in a cross-sectional area or in a (local) volume of the arteria ulnaris and/or the arteria radialis at a second location or position, and to create a second measurement signal on the basis thereof. In FIG. 3, the plethysmographs 330, 340 are schematically shown as ribbons or as ribbon-like devices arranged around the forearm 310. However, different kinds of plethysmographs may also be used, for example such plethysmographs that determine a change in the volume of one or more arteries by way of optics (for example by x-raying the forearm), by performing an impedance measurement on the forearm or by performing a capacitance measurement on the forearm, so as to obtain the first measurement signal and the second measurement signal. Other devices than plethysmographs may also be used for obtaining the first measurement signal and the second measurement signal such that the measurement signals describe a pulse wave within the arteria ulnaris and/or the arteria radialis at various locations along the forearm.

It shall be noted that instead of the forearm 310, an upper arm, a lower leg or a thigh may also be used, for example. Blood pressure measurement may naturally also be performed on other parts of the body of a human being or an animal.

Figure 4:
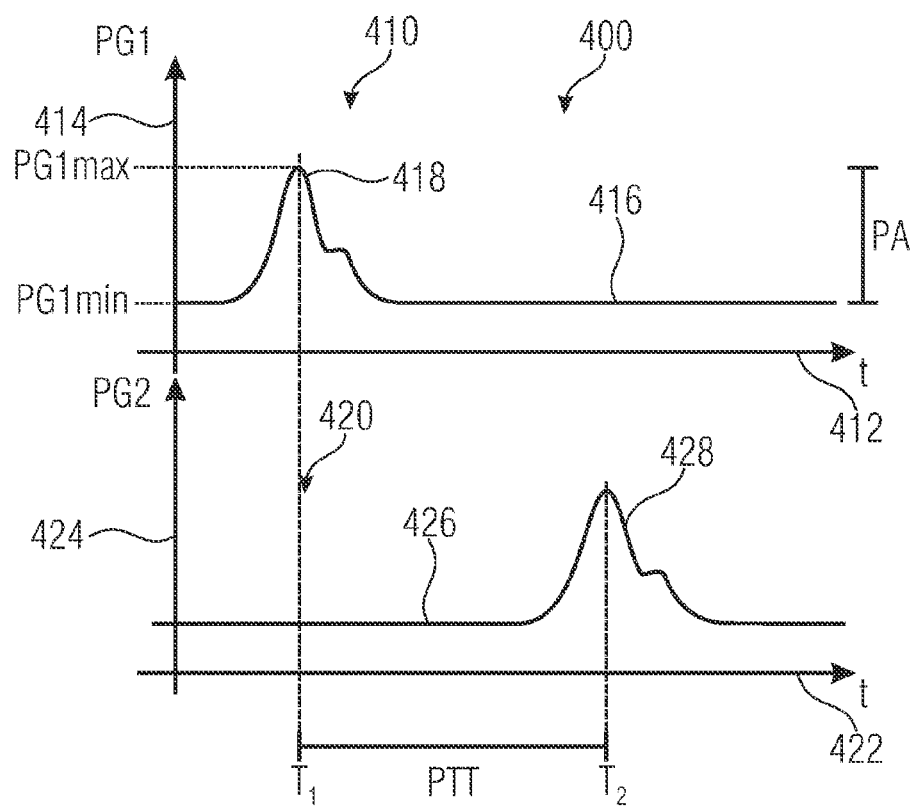
FIG. 4 shows a graphic representation of two plethysmograph signals of two plethysmographs arranged at different locations.

FIG. 4 shows a schematic representation of temporal waveforms, for example of the first plethysmograph 330 (PG 1) and of the second plethysmograph 340 (PG 2). The temporal waveforms may be used, for example, as a basis for calculating a transmit time, or pulse transmit time (also referred to as PTT) and a pulse amplitude (also referred to as PA) in the manner shown. The schematic representation of FIG. 4 is designated by 400 in its entirety. The schematic representation 400 comprises a first signal representation 410 describing, for example, the measurement signal provided by the first plethysmograph 330 (also referred to as PG 1). An abscissa 412 describes the time, for example, and an ordinate 414 describes, in arbitrary units, a quantity of the first measurement signal provided by the first plethysmograph 330, for example. A curve 416 describes a temporal course of the first measurement signal.

The graphic representation 400 comprises a second signal representation 420. The second signal representation 420 comprises an abscissa 422 having the time t plotted thereon, and an ordinate 424 describing, in arbitrary units, a quantity of the second measurement signal provided by the second plethysmograph 340. A curve 426 describes a temporal development of the second measurement signal.

In FIG. 4, for example, the abscissas, or time axes, 412, 422 are mutually aligned.

An amplitude of the first measurement signal may be defined, for example, as a difference between a maximum value PG1max and a minimum value PG1min of the first measurement signal within a specific period of time, as is defined, e.g., in the first signal representation 410.

It can be gathered from the signal representations 410, 420 that e.g. a maximum of the first measurement signal described by the curve 416 occurs at a first point in time T1, whereas a maximum of the second measurement signal described by the curve 426 occurs at a second point in time T2. In this respect it shall be noted that, e.g., the maximum 418 of the first measurement signal and the maximum 428 of the second measurement signal are associated with each other, or belong together, that is they are caused by the propagation of a single pulse wave. A time offset between the maximum 418 of the first measurement signal and the maximum 428 of the second measurement signal here is referred to as a transmit time PTT.

Figure 5:
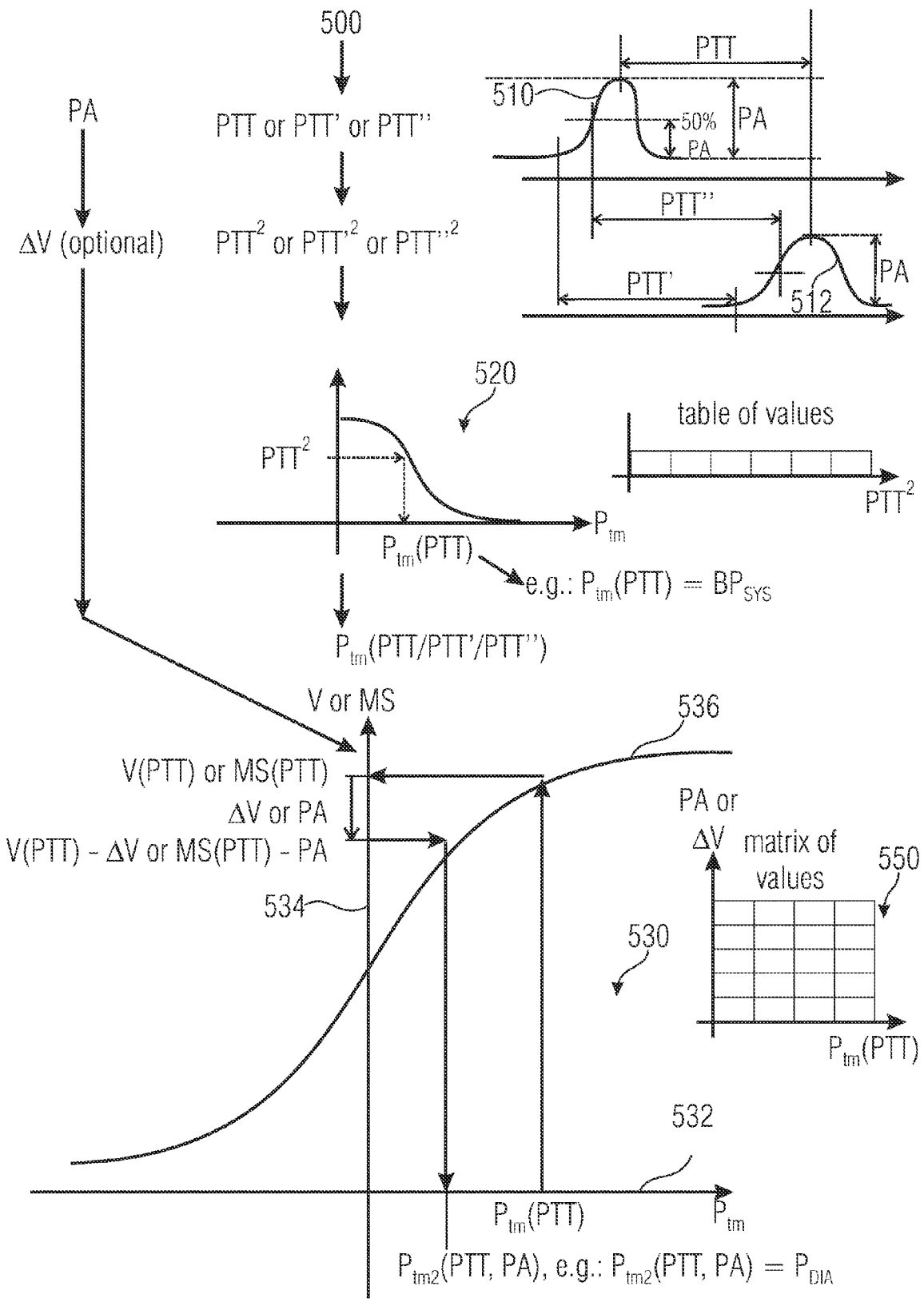
FIG. 5 shows a schematic representation of an approach to determining pressure values on the basis of transmit time information and amplitude information, in accordance with an embodiment of the invention.

What follows is an explanation, by means of FIG. 5, how the pressure gauge or blood pressure gauge described herein, e.g. the pressure gauge 100 of FIG. 1, may determine a pressure value on the basis of the transmit time information (e.g. on the basis of transmit time information 112, also referred to as PTT or PTT' or PTT") and of the amplitude information (e.g. the amplitude information 114, also referred to as PA).

The schematic representation of FIG. 5 is designated by 500 in its entirety and describes, for example, a method as may be performed by the pressure value determiner 120. In other words, the pressure value determiner 120 may be adapted, e.g., to perform the method described by means of FIG. 5.

What follows initially is an explanation of how the transmit time information 112 may be obtained. The transmit time information 112 may be determined, e.g., by evaluating the first measurement signal (which may be generated in the manner discussed herein) and the second measurement signal (which also may be generated in the manner discussed herein). For example, for determining the transmit time information 112, pulses 510, 512 of the first measurement signal (pulse 510) and of the second measurement signal (pulse 512)—which pulses belong together—may be evaluated so as to obtain the transmit time information 112. Pulses that belong together, or are associated with each other, are understood to mean pulses that are caused by the same pulse wave and may be recognized, e.g., by the fact that they are within a specific time interval.

In one embodiment, the transmit time information 112 may describe, for example, how much time passes between a maximum of the first pulse 510 (in the first measurement signal) and a maximum of the second pulse 512 (in the second measurement signal), as is shown in FIG. 5.

In a further embodiment, the transmit time information 112 may describe how much time passes between a start of the first pulse 510 and a start of the second pulse 512. A start of the first pulse 510 may be defined, e.g., as a point in time at which the measurement signal has increased by a certain amount as compared to a quiescent signal value, it being possible for said corresponding specific amount to be defined, e.g., as an absolute value or as a percentage of the signal amplitude PA. For example, the start of the first pulse 510 may be defined as a point in time at which the first measurement signal increases by 5% or 10% of the signal amplitude PA, starting from a quiescent value. A start of the second pulse 512 may be defined accordingly. The corresponding transmit time information PTT', which describes the time passing between the start of the first pulse 510 and the start of the second pulse 512, may describe, e.g., a duration that is longer or shorter than a partial duration between maxima of the pulses 510, 512, since shapes of the pulses 510, 512 may indeed differ.

In a further embodiment, the transmit time information 112 may describe, e.g., a duration between a center of a rising edge of the first pulse 510 and a center of a rising edge of the second pulse 512. The center of the rising edge is understood to mean, for example, a point in time at which a pulse has risen by 50% of the associated signal amplitude PA, starting from a quiescent value. The corresponding definition is illustrated in FIG. 5. The resulting value of the transmit time information 112 is designated by PTT".

It shall also be noted that the transmit time information values PTT, PTT' and PTT" may be used alternatively. In other words, it is sufficient for the transmit time information 112 to describe one of said values PTT, PTT', PTT".

In accordance with an embodiment, the transmit time value described by the transmit time information may be squared in a first step so as to obtain a first squared transmit time value $PTT^2$ or $PTT'^2$ or $PTT''^2$. In a second step, for example, an associated first blood pressure value $P_{tm}$ (PTT) may be determined on the basis of the squared transmit time value while using a first mapping 520. The first mapping 520 may thus describe a relationship between the squared transmit time value $PTT^2$ and an associated transmural pressure $P_{tm}$ (PTT). The notation "( . . . )" here signifies "as a function of . . . " or "depending on . . . " or "belonging to . . . ".

The first mapping 520 may be described, for example, by a closed expression describing, e.g., a Gaussian function, or by parameters of a closed expression. Alternatively, the first mapping 520 may also be described by a suitable table of values, for example. Of course, other possibilities of describing a first mapping may also be employed. The first mapping 520 may be realized by an analog circuit or by a digital circuit (e.g. a digital arithmetic circuit). Many different possibilities may thus be used in this context.

It shall be noted that the concept described in FIG. 5 may be employed for a blood pressure gauge. For example, if the transmit time information or the corresponding transmit time value describes the duration PTT between the maxima of the pulses 510, 512, one may obtain, e.g., as a first pressure value, or blood pressure value, a systolic blood pressure value, a diastolic blood pressure value or a mean blood pressure value by means of the first mapping 520 on the basis of the squared transmit time value. If the transmit time value used is the transmit time value PTT', the first mapping 520 may provide, as the first pressure value, a systolic blood pressure value, a diastolic blood pressure value or a mean blood pressure value, for example. If the transmit time value used is the transmit time value PTT", the first mapping 520 will provide, as the first pressure value, at least approximately, a systolic blood pressure value, a mean blood pressure value or a diastolic blood pressure value, for example.

One may generally state that by applying the first mapping 520 to the transmit time value used (PTT or PTT' or PTT"), the first pressure value obtained is a corresponding pressure value $P_{tm}$(PTT) or $P_{tm}$(PTT') or $P_{tm}$(PTT").

A third step may then comprise employing the amplitude information 114 or a corresponding amplitude value (PA) as well as the first pressure value $P_{tm}$(PTT) or $P_{tm}$(PTT') or $P_{tm}$(PTT") in order to obtain a second pressure value.

What follows is a description, by means of FIG. 5, of how the method may be performed if, e.g., the transmit time information 112 describes the transmit time value PTT (i.e. the duration between maxima of two pulses 510, 512).

A second mapping 530 may describe, e.g., a relationship between a pressure $P_{tm}$ and a local diameter, a local cross-sectional area or a local volume V. Alternatively, the second mapping 530 may also describe a relationship between the pressure $P_{tm}$ (within a flexible fluid conductor) and an associated measurement signal MS (for example of a corresponding sensor or plethysmograph). In some embodiments, the measurement signal MS of the sensor may be at least approximately proportional to the volume V of the elastic fluid conductor, so that a mapping which describes a relationship between the pressure $P_{tm}$ and the local volume V is at least approximately identical, in terms of quality, with a mapping which describes a relationship between the pressure $P_{tm}$ and the measurement signal MS. Thus, the second mapping 530 overall describes a relationship between two pressure values and an amplitude of the measurement signal—even when the second mapping primarily describes a relationship between pressure and volume.

In some embodiments, an amplitude PA of a measurement signal may be at least approximately proportional to a change in volume $\Delta V$.

In some embodiments, the second mapping may directly describe an association between an amplitude PA of a measurement signal and a pressure difference (e.g. between the first pressure value and the second pressure value).

In some embodiments, the second mapping may describe an association between a change in volume $\Delta V$ and a pressure difference (e.g. between the first pressure value and the second pressure value). Additionally, the second mapping may describe, in this case as a scaling, a relationship (for example a proportionality) between an amplitude PA of the measurements signal and the change in volume $\Delta V$ (e.g. by a corresponding proportionality constant referred to as a "factor").

In some embodiments, the second mapping may describe an association between the first pressure value and the second pressure value as a function of an amplitude PA of a measurement signal. The difference between the first pressure value and the second pressure value in this context is dependent, for example, not only on the first amplitude PA, but also on the first pressure value.

In some embodiments, the second mapping may describe an association between the first pressure value and the second pressure value as a function of a change in volume $\Delta V$ of a measurement signal. The difference between the first pressure value and the second pressure value is dependent, e.g., not only on the amplitude PA, but also on the first pressure value. Additionally, the second mapping may describe, in this case as a scaling, a relationship (for example a proportionality) between an amplitude PA of the measurements signal and the change in volume $\Delta V$ (e.g. by a corresponding proportionality constant referred to as a "factor").

It is apparent from the above illustrations that there is a multitude of possibilities of describing a relationship between the first pressure value, the second pressure value and the amplitude information in the form of a mapping. All of the possibilities described, and other possibilities not described here, may be utilized in the device and method described herein.

A potential mapping that may be used as the "second mapping" is described at reference numeral 530 in FIG. 5. For illustration purposes, for example, a pressure $P_{tm}$ is plotted on an abscissa 532. A quantity of a local volume V or a quantity of a measurement signal MS is plotted on an ordinate 534, for example. A curve 536 describes, e.g., a relationship between the pressure $P_{tm}$ and a value of the local volume V, or a relationship between the pressure $P_{tm}$ and a value of the measurement signal MS.

In the embodiment described by means of FIG. 5, the pressure $P_{tm}$ determined in a second step (also referred to as $P_{tm}$(PTT) herein), for example, may be mapped to a volume value V(PTT) or to a measurement signal value MS(PTT) while using the second mapping 530. For example, if the amplitude value PA is known, a modified measurement signal value MS(PTT)−PA may consequently be determined. Alternatively, the amplitude value PA may be mapped to a change-in-volume value ΔV. Thus, a modified volume value V(PTT)−ΔV may be determined. Thus, the pressure value $P_{tm2}$(PTT, PA) may be determined, while using the second mapping, on the basis of the value MS(PTT)−PA and/or V(PTT)−ΔV, which has been obtained accordingly.

The second mapping 530 may be used, for example, to obtain the volume value V or the measurement signal MS belonging to the pressure value $P_{tm}$(PTT) or to obtain the second pressure value $P_{tm2}$ belonging to the modified volume value V(PTT)−ΔV or modified measurement signal value MS(PTT)−PA, as is shown in FIG. 5.

A relationship, or a difference, between $P_{tm}$(PTT) and $P_{tm2}$(PTT, PA) is dependent, in accordance with the second mapping 530, not only on the measurement signal amplitude PA or on the change in volume ΔV, but also on the first pressure value $P_{tm}$(PTT). This dependence results from the non-linearity of the curve 530, which in turn reflects the properties of an elastic fluid conductor, such as a blood vessel, for example.

It shall also be noted that in the embodiment described by means of FIG. 5, the second pressure value may be a diastolic pressure value $P_{DIA}$, for example.

It shall also be noted that the second mapping 530 may be represented in various forms. For example, the second mapping may be described by a parameterized closed function rule.

Alternatively, the second mapping may be described by a table of values or an association table describing an association between pressure values and volume values, or between pressure values and amplitude values.

Alternatively, the second mapping may be represented by a matrix of values which associates, e.g., different values of the second pressure value $P_{tm2}$ with different combinations consisting of the first pressure value $P_{tm}$(PTT) and the measurement signal amplitude PA. The matrix of values shown at reference numeral 550 in FIG. 5 by way of example may describe, e.g., that a difference between the first pressure value and the second pressure value is dependent not only on the measurement signal amplitude PA or the change in volume ΔV, but also on the first pressure value $P_{tm}$(PTT) itself.

While a description of the second mapping 530 by a curve 536, by a table of values or by a matrix of values 550 was described, for example, with reference to FIG. 5, the second mapping 530 may obviously also be realized differently. An analog circuit may be devised, for example, which realizes the second mapping 530. Other forms of realization are also possible, for example by evaluating a course of a function described in a closed form, by employing several tables of values or by taking similar measures.

Figure 6A:
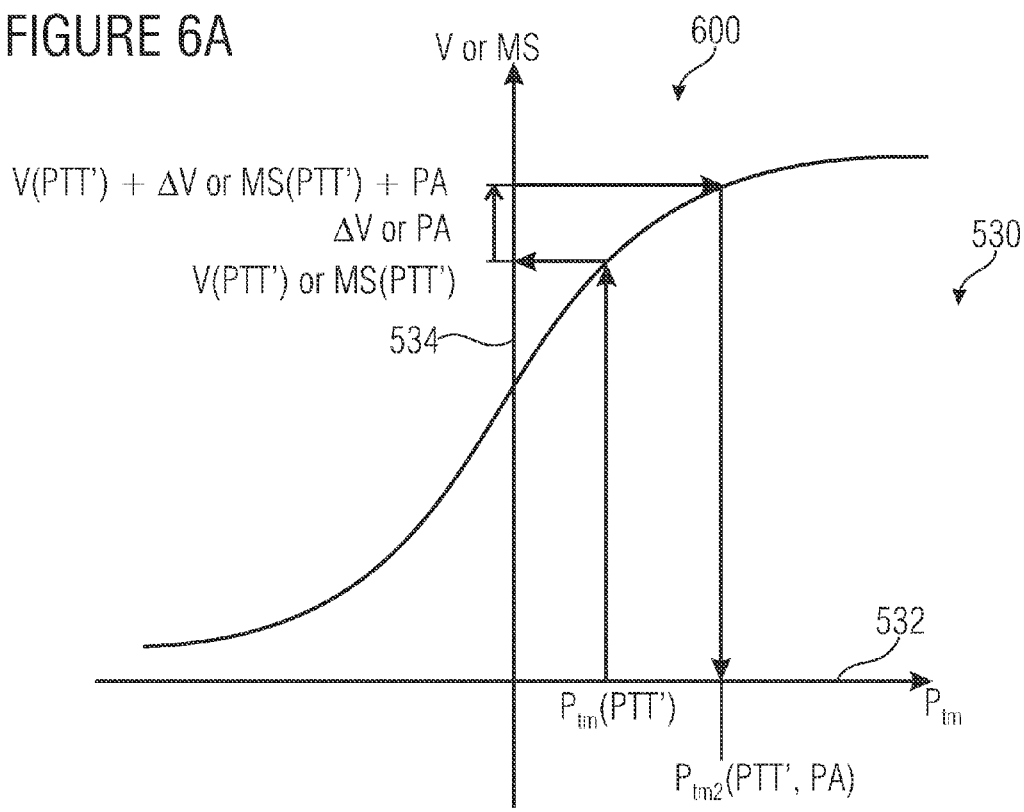
FIG. 6a shows a schematic representation of an approach to determining a second pressure value on the basis of a first pressure value and on amplitude information, in accordance with an embodiment of the invention.
Figure 6B:
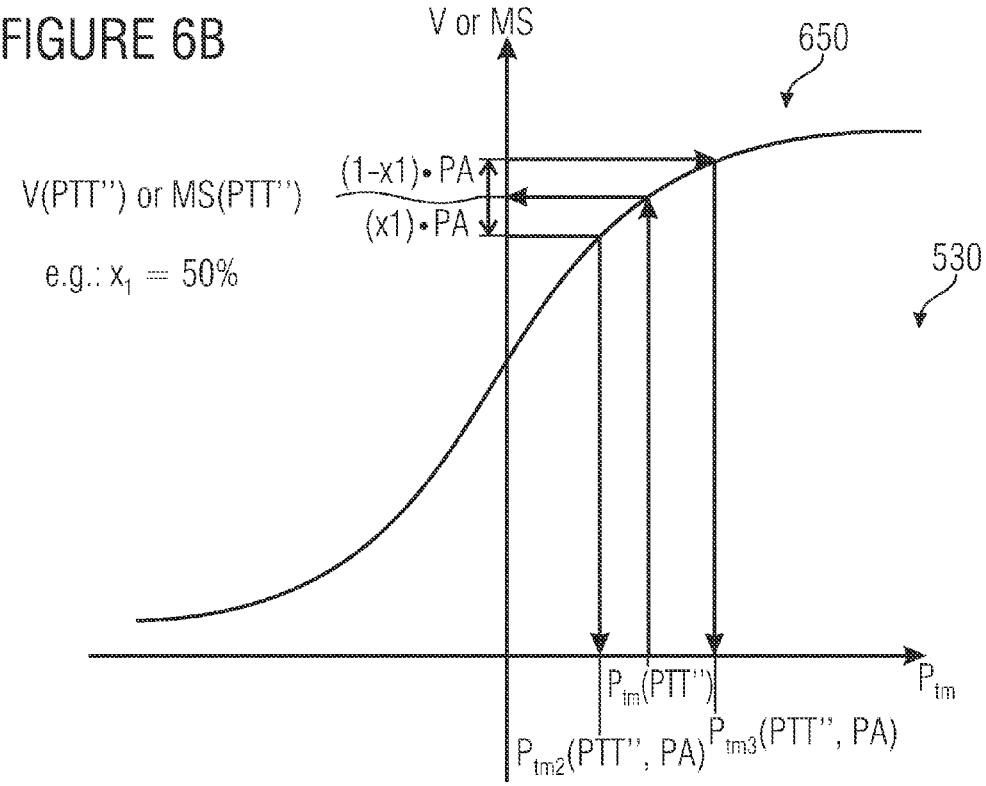
FIG. 6b shows a schematic representation of an approach to determining a second pressure value and a third pressure value on the basis of a first pressure value and on amplitude information, in accordance with an embodiment of the invention.

What follows is a brief description, by means of FIGS. 6a and 6b, of how in some alternative embodiments, the second pressure value may be determined with the aid of the first pressure value. In other words, FIG. 6a shows a schematic representation describing a determination of the second pressure value on the basis of the first pressure value while using the measurement signal amplitude. The graphic representation of FIG. 6a is designated by 600 in its entirety.

The approach described in FIG. 6a may replace the third step as was described with reference to FIG. 5, for example if the first pressure value obtained is at least approximately a diastolic pressure value. It shall be assumed here, for example, that the value $P_{tm}$(PTT') designates a diastolic pressure value. However, in some embodiments, $P_{tm}$(PTT) or $P_{tm}$(PTT"), too, may describe a corresponding diastolic pressure value. It shall also be noted that identical means or features or steps in FIGS. 5, 6a and 6b are designated by identical reference numerals.

As may be readily gathered from FIG. 6a, an associated volume value or measurement signal value (e.g. V(PTT') or MS(PTT')) may be determined with regard to the first, diastolic pressure value (for example $P_{tm}$(PTT')) while using the second mapping 530. Accordingly, a modified volume value (e.g. V(PTT')+ΔV) or a modified measurement signal value (e.g. MS (PTT')+PA) may be determined, from which, in turn, the second pressure value (e.g. $P_{tm2}$(PTT', PA)) may be determined, for example by means of renewed evaluation of the second mapping. The corresponding approach is readily apparent from FIG. 6a.

FIG. 6b shows a schematic representation describing a determination of the second pressure value and of a third pressure value on the basis of the first pressure value while using the measurement signal amplitude. The graphic representation of FIG. 6b is designated by 650 in its entirety. The approach described with reference to FIG. 6b may replace the third step as was described, e.g., by means of FIG. 5, for example when the first pressure value obtained is a mean pressure value. It shall be assumed here, for example, that the value $P_{tm}$(PTT") designates a mean pressure value. However, in some embodiments, $P_{tm}$(PTT) or $P_{tm}$(PTT'), too, may describe a corresponding mean pressure value.

As is readily apparent from FIG. 6b, an associated volume value (e.g. V(PTT")) or measurement signal value (e.g. MS(PTT")) may be determined, for example, with regard to the first pressure value $P_{tm}$(PTT') (or ($P_{tm}$(PTT) or $P_{tm}$(PTT")) while using the second mapping 530. Accordingly, an upper volume value (e.g. V(PTT")+(1−$x_1$)·ΔV) or an upper measurement signal value (e.g. MS (PTT")+(1−$x_1$) may be determined, for example. While applying the second mapping 530 again, the third pressure value (e.g. $P_{tm3}$(PTT", PA)) may be determined, for example, from the upper volume value or the upper measurement signal value. In addition, a lower volume value (e.g. V(PTT")−($x_1$·ΔV) or a lower measurement signal value (e.g. MS(PTT")−$x_1$·PA) may be calculated, for example. The second pressure value (e.g. $P_{tm2}$(PTT", PA)) may then be determined from the lower volume value or the lower measurement signal value, for example by re-using the second mapping 530. The approach may be readily gathered from FIG. 6b.

When employing the approach described with reference to FIG. 6b, both the second pressure value and the third pressure value may be determined, for example, on the basis of a measurement of a pulse transmit time PTT, PTT' or PTT", which in some embodiments represents a mean pressure value, and on the basis of a measurement of the pulse amplitude PA. In one embodiment, measurement of the transmit time value PTT" is particularly reliable and/or precise, since the pulses 510, 512 have a particularly large inclination in an area that is close to their (in terms of amplitude) mean value. The value $x_1$ may indicate that one of the pulses 510, 512 is above a quiescent value by $x_1$·PA at a point in time at which the transmit time value PTT" is measured. Using the method described with reference to FIG. 6b, a systolic and a diastolic pressure value may thus be determined, for example, in which context it is not necessary to determine a transmit time value PTT between the maxima of the pulses 510, 512. Rather, it is sufficient to determine the transmit time value PTT".

Figure 7:
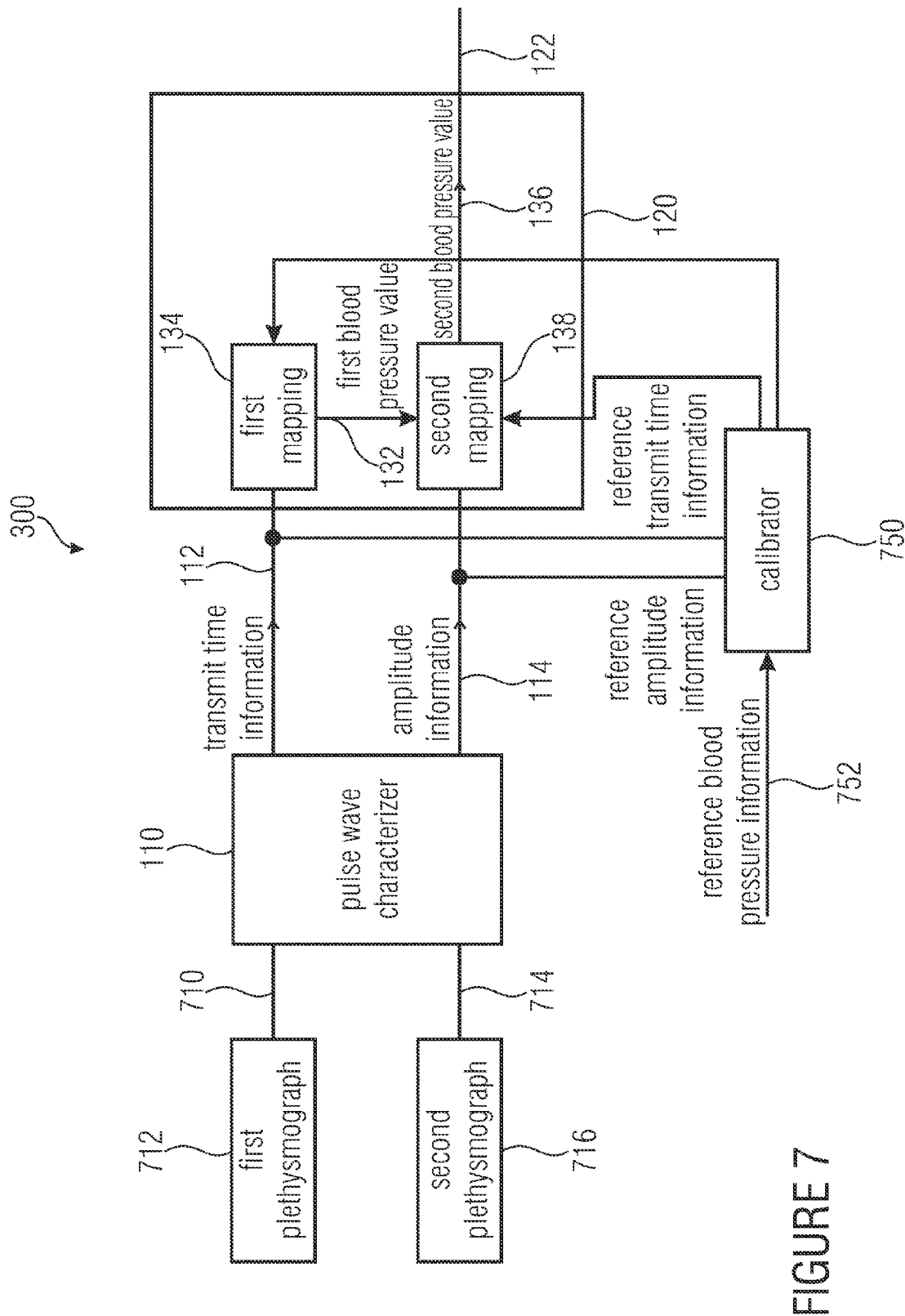
FIG. 7 shows a block diagram of a pressure gauge in accordance with a further embodiment of the invention.

FIG. 7 shows a block diagram of a pressure gauge in accordance with an embodiment of the invention. The pressure gauge of FIG. 7 is designated by 700 in its entirety. The pressure gauge 700 may be a blood pressure gauge, for example, but may also be a pressure gauge for utilization in industrial or other pressure measurement.

The pressure gauge 700 of FIG. 7 is very similar to the pressure gauge 100 of FIG. 1, so that identical means, features or signals are designated by identical reference numerals in FIGS. 1 and 7.

Just like the pressure gauge 100, the pressure gauge 700 may be configured, for example, to receive a first measurement signal 710 from a first plethysmograph 712, and a second measurement signal 714 from a second plethysmograph 716. The first measurement signal 710 and the second measurement signal 714 may be supplied to the pulse wave characterizer 110, for example, which pulse wave characterizer 110 may be configured to determine the transmit time information 112 and the amplitude information 114 on the basis of the measurement signals 710, 714. The plethysmographs 712, 716 may also be part of the pressure gauge in some embodiments. In other embodiments, the plethysmographs 712, 716 may also be separate from the pressure gauge and be produced or supplied by a different manufacturer, for example. The plethysmographs 712, 716 may be replaced by other measurement means that are suitable to provide measurement signals 710, 714 which describe a propagation of, e.g., a pulse wave. One of the measurement signals 710, 714 may be provided, in a medicinal application, by an electrocardiograph or by a means for measuring thorax impedance.

With the pressure gauge 700, a calibrator 750 is provided which is configured to suitably set, or adjust, the first mapping 134 and the second mapping 138 so as to achieve calibration of the pressure gauge 700. In other words, in the present embodiment, the first mapping 134 and the second mapping 138 are not fixedly defined, but may be set, for example, by specifying parameters of a closed function description (e.g. of parameters a, b of a Gaussian function of the form $PTT^2=a\cdot\exp(-b\cdot P_{tm}^2)$). Alternatively, the first mapping 134 may also be represented by a variable table of values that may be stored in a memory, for example. The entries of the table of values may be directly obtained, for example, within a framework of a calibration (e.g. by entering pairs of measured values). The entries of the table of values which describes the first mapping may alternatively be obtained, e.g., by scaling a predefined function (for example the Gaussian function indicated above that is parameterized with parameters a and b). The predefined function may be described, for example, by a closed function rule or be stored in a fixedly defined table of values.

The second mapping 138 may be adjustable, for example. The second mapping 138 may be described, for example, by a parameterized closed function rule or by a table of values or a matrix of values. There are various forms of description of the second mapping 138, as was already explained above.

The calibrator 750 is configured to suitably set the first mapping 134 and the second mapping 138 in a calibration. To this end, the calibrator 750 receives during a calibration e.g. associated values of the transmit time information 112, of the amplitude information 114 and of reference pressure information or reference blood pressure information 752. The reference blood pressure information 752 describes, e.g., a blood pressure value measured by a further pressure measurement device or blood pressure measurement device under the same external conditions (e.g. in a timely manner) under which the associated values of the transmit time information 112 and of the amplitude information 114 were determined as well.

Figure 8A:
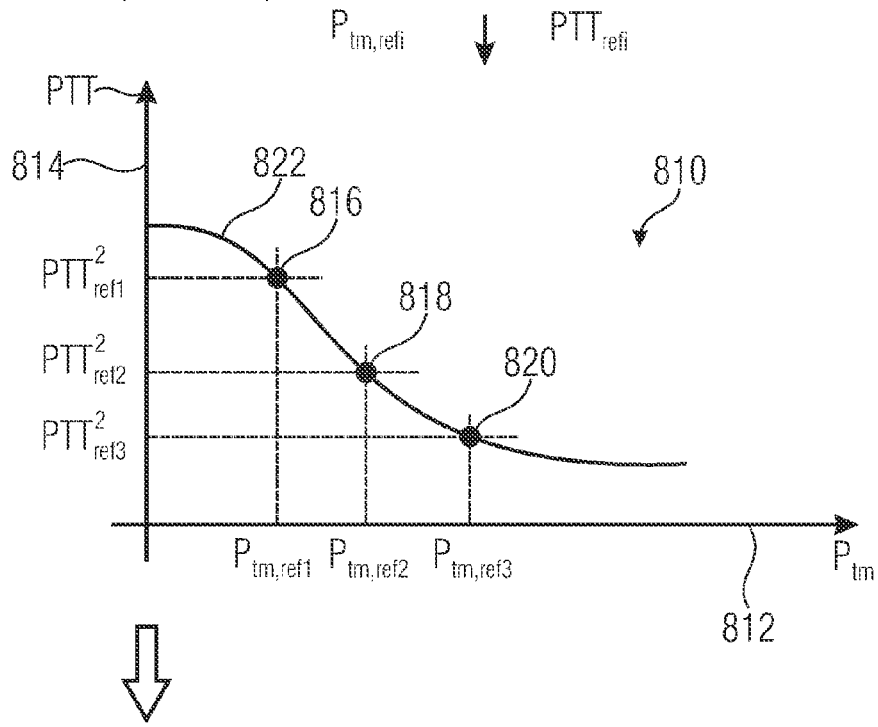
FIG. 8a shows a first part of a schematic representation of an approach to calibrating a pressure gauge, in accordance with an embodiment of the invention.
Figure 8A:
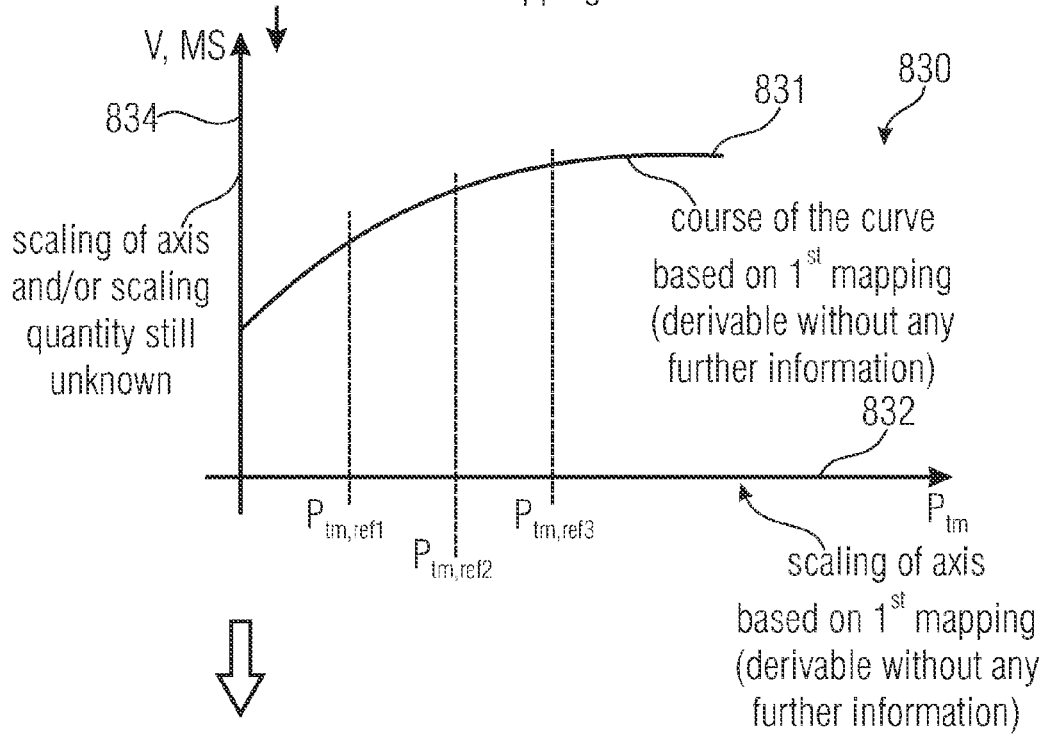
Figure 8B:
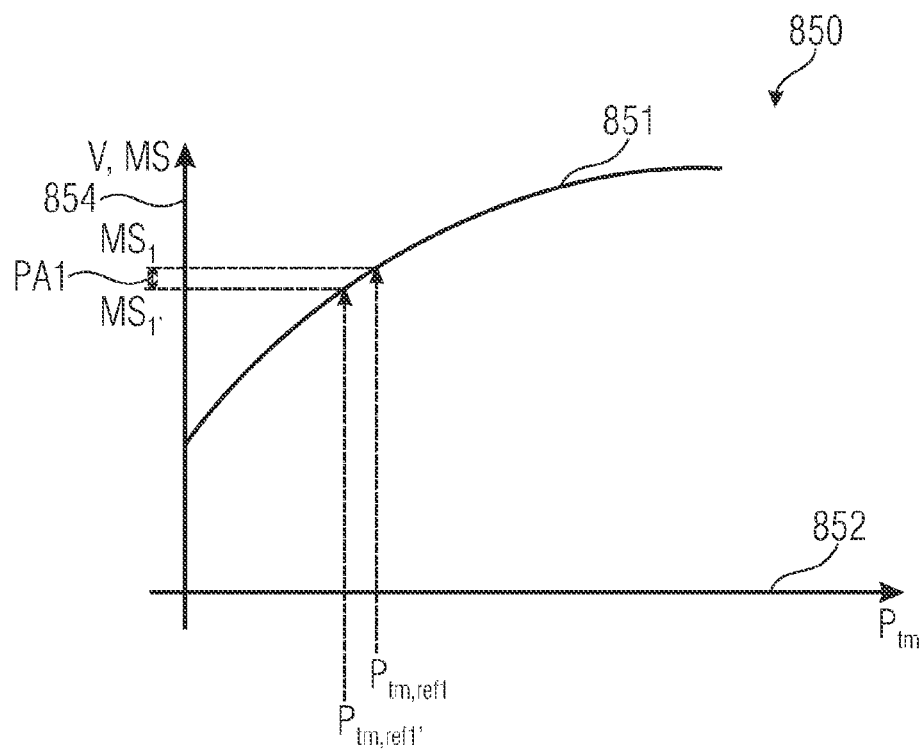
FIG. 8b shows a second part of a schematic representation of an approach to calibrating a pressure gauge, in accordance with an embodiment of the invention.

Details regarding an approach in the calibration will be described below with reference to FIGS. 8a and 8b. In other words, FIGS. 8a and 8b show a schematic representation of the approach in the calibration.

A schematic representation 810 shows how the first mapping may be determined, or specified, on the basis of several pairs of measured values of the reference pressure information 752 (also referred to as reference pressure values here) and of the transmit time information 112 (also referred to as reference transmit time values here). In one embodiment, a qualitative course of the first mapping is given, e.g., by a predefined closed function rule comprising one or more variable parameters (e.g. by a function rule describing a Gaussian curve, while parameters a, b are still undefined). Alternatively, a qualitative course of the first mapping may also be described by a predefined table of values that is adapted to the measured reference pressure values or reference transmit time values by means of corresponding scaling.

The first schematic representation 810 illustrates determination of the first mapping by means of a representation of the mapping as a curve. A pressure $P_{tm}$ is plotted, for example, on an abscissa 812, and a square of a transmit time value ($PTT^2$) is plotted on an ordinate, for example. A qualitative course of the mapping 810 may be specified, for example, by a Gaussian-type relationship between the pressure value $P_{tm}$ and an associated squared transmit time value $PTT^2$, wherein the following may apply at least approximately: $PTT^2=a\cdot\exp(-b\cdot P_{tm}^2)$. The mapping 810 shows pairs of associated measurement values represented as points 816, 818, 820. Thus, the points 816, 818, 820 represent pairs consisting of a measured reference pressure value and an associated measured reference transmit time value. The parameters of the above-mentioned Gaussian-type relationship that is represented by a line or curve 822 are set, during the calibration, such that the Gaussian-type course deviates as little as possible from the pairs of reference measurement values. In other words, the parameters a, b of the Gaussian course are selected such that the line 822 extends as close as possible to the points 816, 818, 820. To this end, a method of minimizing squares of errors may be employed, for example, as is well-known. In addition, it shall be noted that as few as two pairs of reference measurement values are sufficient to specify two parameters of the Gaussian-type relationship. However, if more pairs of reference measurement values are known, accuracy may be improved, since errors may be averaged out.

In summary, it may be stated that the first mapping may be specified on the basis of a plurality of pairs of reference measurement values (e.g. reference pressure values and reference transmit time values).

In a second step of the calibration, a qualitative course of the second mapping may be specified, for example, as is indicated at reference numeral 830. The second mapping is described, for example, by a course of a curve 831 that may be represented by a closed function rule, by a table of values or in any other way. In FIG. 8a, an abscissa 832 describes a pressure $P_{tm}$, whereas an ordinate 834 describes, e.g., a volume or a measurement signal (e.g. from a plethysmograph). In one embodiment in accordance with the invention, a qualitative course of the second mapping is specified on the basis of a qualitative course of the first mapping. For example, in some embodiments, the qualitative course of the second mapping may be determined (e.g. without using any further information) from the qualitative course of the first mapping in that, e.g., the first mapping is integrated with regard to the pressure $P_{tm}$. In this respect, the abscissas 812, 832 may be scaled in the same manner. In some embodiments, scaling of the ordinate 834 is specified separately, however, and is not specified directly by means of the course of the first mapping.

At reference numeral 850, FIG. 8b shows a potential procedure in specifying a quantitative course (i.e., for example, a scaling) of the second mapping. The second mapping, in turn, is represented by a course of a curve 851. An abscissa 852 describes the pressure $P_{tm}$, and an ordinate 854 describes a volume of an elastic fluid conductor or a value of a corresponding measurement signal (e.g. of the first measurement signal or of the second measurement signal). In accordance with an embodiment, two pressure values in different phases of the pulsating flow are determined for a pulsating fluid flow. For example, a maximum value of a pressure and a minimum value of the pressure may be determined under essentially unchanged conditions of the pulsating flow. In one embodiment, the maximum value of the pressure and the minimum value of the pressure may be related to a single period of the essentially periodically pulsating flow, or be related to a small number of, e.g., of a maximum of five or ten successive periods of the pulsating flow. A corresponding maximum pressure value is designated by $P_{tmref1}$, for example, and a corresponding associated minimum pressure value is designated by $P_{tmref1'}$, for example. While using the qualitative course of the second mapping, which course may indeed have been previously determined, it will be determined, for example, which values (e.g. volume values V) or which difference value (e.g. volume difference $\Delta V$) are associated with the pressure values $P_{tmref1}$, $P_{tmref1'}$ in accordance with the second mapping (which may still be unscaled, for example).

The second mapping, which is still unscaled, may then be scaled, e.g., such that a difference between a measurement signal value MS1 associated with the pressure value $P_{tmref1}$ by the scaled second mapping, and a measurement signal value MS1' associated with the pressure value $P_{tmref1'}$ by the scaled second mapping is equal to the amplitude value PA1. The amplitude value PA1 is, e.g., an amplitude value of an actually measured measurement signal for a pulse comprising the pressure values $P_{tmref1}$, $P_{tmref1'}$.

However, the scaling may also be effected in that a scaling factor is determined which describes, e.g., a ratio between an amplitude PA of a measurement signal and an associated change in volume. The corresponding scaling factor for a scaling rule describing an association between an amplitude PA and a pressure difference may be part of the second mapping, for example.

In summary, it may therefore be stated that a course of the first mapping may be determined, e.g., while using reference pressure values $P_{tmref1}$, $P_{tmref2}$, $P_{tmref3}$, the pressure values mentioned belonging to different pulses of the pulsating flow, the different pulses of the pulsating flow being measured under different pressure conditions. A qualitative course of the second mapping is specified on the basis of a qualitative or quantitative course of the first mapping, for example by integrating the first mapping over the pressure. Such an approach entails that the characteristic points (e.g. maxima, minima or mean values) of pulse waves may be evaluated, respectively, to specify the first mapping and the quantitative course of the second mapping. However, scaling of the second mapping is effected by evaluating an amplitude of a measurement signal for a pulse or for the time period comprising pulses with at least approximately identical pressure conditions. By utilizing a pulse amplitude for scaling the second mapping, one may avoid, for example, that an absolute value of the measurement signals that may change over time due to a steady-component drift influences the scaling. In some embodiments, DC signal components of the measurement signals may even be neglected or suppressed due to the corresponding scaling of the second mapping, without the measurement accuracy being substantially deteriorated. Thus, some embodiments of the invention enable determining the pressure on the basis of only alternating components of the measurement signals.

Figure 8C:
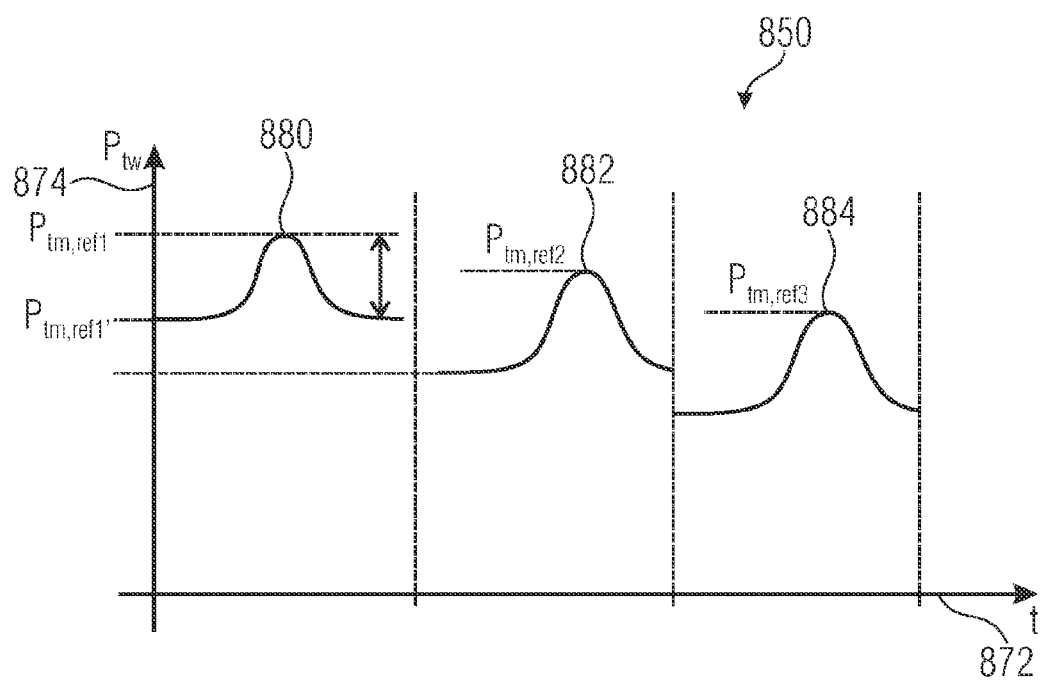
FIG. 8c shows a schematic representation of different pulse waves that may be used for calibrating a pressure gauge.

FIG. 8c shows a schematic representation of several pulses that may be evaluated in a calibration, for example. The schematic representation of FIG. 8c is designated by 870 in its entirety. An abscissa 872 describes a time in arbitrary units, and an ordinate 874 describes a pressure $P_{tm}$. A first pulse 880 occurs, e.g., at a high pressure level, a second pulse 882 occurs, e.g., at a medium pressure level, and a third pulse 884 occurs, e.g., at a low pressure level. Corresponding pressure levels are designated accordingly in FIG. 8c.

Figure 9:
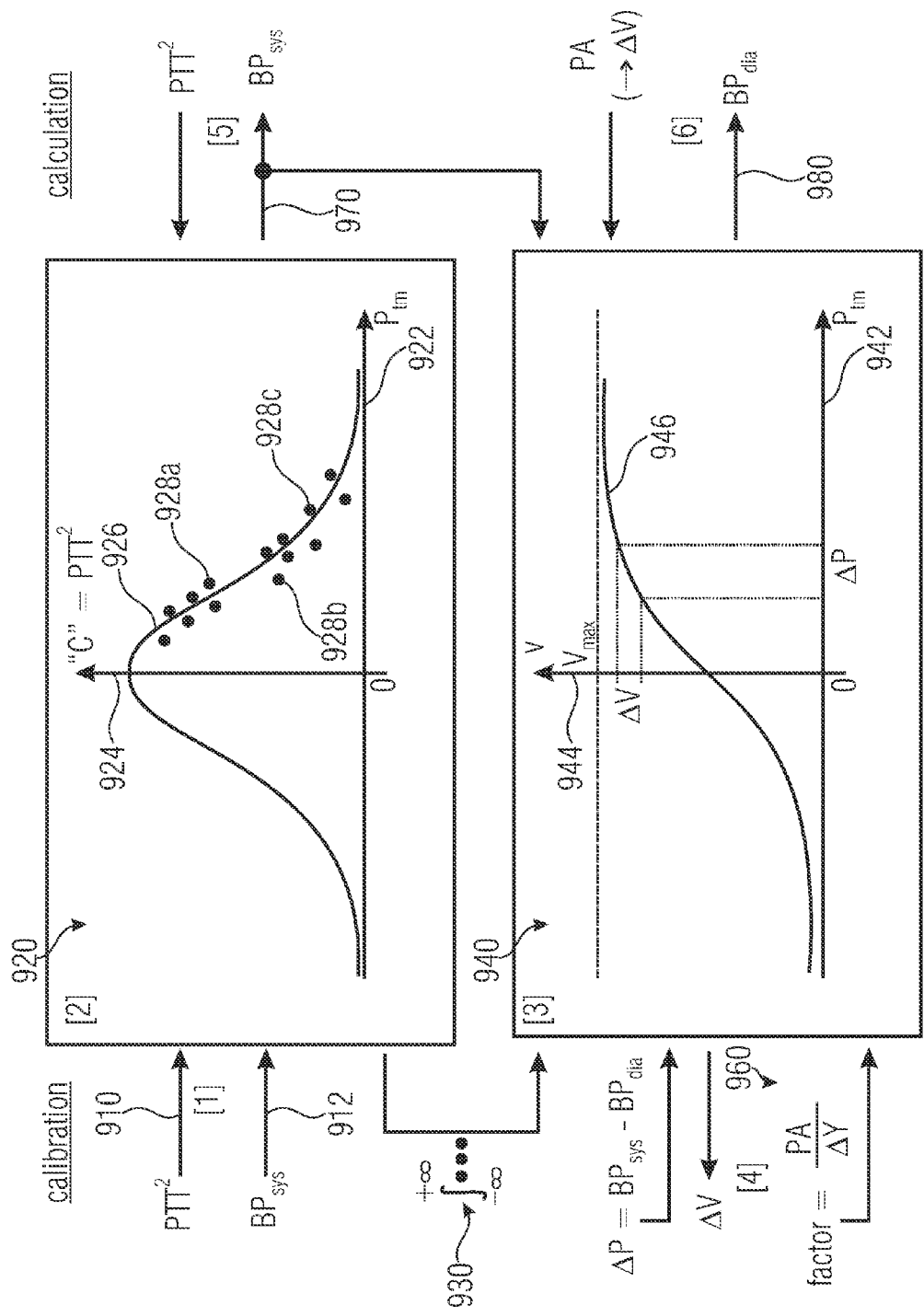
FIG. 9 shows a summarized schematic representation of an approach in a calibration of a pressure gauge and in a calculation of a pressure value.

A further embodiment in accordance with the invention will be briefly explained below with reference to FIG. 9. FIG. 9 shows an overview of individual components of a blood pressure model and of individual signal processing steps.

A system in accordance with an embodiment of the invention is based, in its application—e.g. for non-invasive, continuous blood pressure measurement without cuff—on the parameters of pulse wave transmit time (PTT) and pulse amplitude (PA).

Both parameters, in turn, are based on, for example, a time-synchronous derivation of plethysmograms of two spaced-apart plethysmographs arranged, for example, on a forearm of a patient. A pulse amplitude may be determined, e.g., from one of the two plethysmograms for each heartbeat (beat-by-beat). The pulse wave transmit time may be calculated or determined, for example, as a temporal difference between maxima (or other prominent or characterized points) of the two temporally offset plethysmograph pulse waves. Details on this may be gathered from FIGS. 3 and 4, for example.

The parameters of pulse wave transmit time (PTT) and pulse amplitude (PA) are mapped, in this method, to a systolic blood pressure and/or a diastolic blood pressure, for example with the help of a model of a vessel, it being possible for specific physiological laws to be taken into account. For example, a ratio between a volume V and a corresponding transmural pressure $P_{tm}$ of a vessel section observed is defined by its individual pressure/volume diagram, which may be readily represented as a sigmoid function of the volume over the pressure.

An inclination in the pressure/volume diagram (e.g. a curve describing a relationship between pressure and volume) is a so-called "compliance" (elastic resilience), for example, i.e. a measure of an expansibility of the vessel (or the blood vessel or the fluid conductor), which results in a pressure/compliance diagram as a first derivation of the pressure/volume diagram. A so-called "Bramwell-Hill equation"—a modification of a Moens-Korteweg equation from the field of fluid mechanics—also plays an important part, since it describes a relationship between a pulse wave velocity and an elasticity modulus of a pipe (or fluid conductor) and, thus, a relationship between the pulse wave transmit time and the compliance C of a section of a vessel. For example, the following relationship between the squared transmit time value $PTT^2$ and the compliance C is true at least approximately:

$$PTT^2 = const.*C,$$

wherein "const." designates a constant, for example.

Prior to calculating a blood pressure equivalent by means of the pulse wave transmit time PTT and the pulse amplitude PA, a model of a vessel is individually adapted to the patient and calibrated in that various systolic and diastolic blood pressure values are measured (e.g. auscultatorily or oscillometrically) along with their corresponding pulse wave transmit times and pulse amplitudes.

A Gaussian pressure/compliance equivalent curve which underlies the (observed) section of the vessel and is at least approximately Gaussian-shaped may be approximated, for example by means of a least-mean-squares method, from the systolic blood pressure values and the associated compliance values or $PPT^2$ values (in the schematic representation of FIG. 9 designated by 910, 912 or by [1]).

The pressure/compliance equivalent curve is represented in FIG. 9 in a coordinate system comprising an abscissa 922 which describes the pressure $P_{tm}$ and an ordinate 924 which describes the compliance "C" or a square of the pulse wave transmit time $PTT^2$. The pressure/compliance equivalent curve is described, e.g., by one or more parameters that are specified, for example, within the framework of the calibration such that the pressure compliance equivalent curve approximates sufficiently well a plurality of pairs of systolic blood pressure values and associated compliance values, which are shown by points 928a, 928b, 928c.

By integrating (e.g. over the pressure $P_{tm}$) the Gaussian pressure compliance equivalent curve (which is represented to be symbolic at reference numeral 930, for example), there is, for example in a next step, a corresponding sigmoidal pressure/volume equivalent curve 940 (also referred to by [3]).

A sigmoidal curve or sigmoid function, also referred to as a "swan neck function" or "S-shaped function", is, e.g., a mathematical function having an S-shaped course of the function. Generally, a sigmoid function is, e.g., a limited and differentiable real function having a positive or negative first derivation and precisely one point of inflexion. For example, the integral of a smooth, positive function comprising a "peak" (e.g. of the Gaussian error distribution curve), in turn, is a sigmoid function.

With regard to the pressure/volume equivalent curve, it is to be stated that same is represented in FIG. 9 by a curve 946 in a coordinate system comprising an abscissa 942 describing the pressure $P_{tm}$ and an ordinate 944 describing, e.g., a local volume of a blood vessel or of an elastic fluid conductor. A lower bound of the pressure/volume equivalent curve is at V=0, for example, and a maximum of the pressure/volume equivalent curve is at $V=V_{max}$, for example.

For example, the pressure/volume equivalent curve enables associating a change in pressure ΔP with a change in volume ΔV, or vice-versa. The relationship between the change in volume ΔV and the change in pressure ΔP is actually pressure-dependent due to the non-linearity of the pressure/volume equivalent curve.

By means of a systolic/diastolic blood pressure value pair and its difference, the so-called pulse pressure ΔP, a ratio (designated, e.g., by [4] or 960) between the associated measured pulse amplitude and the corresponding volume difference ΔV in the pressure/volume equivalent diagram may finally also be determined so as to be able to map the pulse amplitude (e.g. an amplitude PA of the measurement signal) to a volume difference ΔV at a later point in time (e.g. during pressure measurement or blood pressure measurement), for example.

For example a systolic and a diastolic blood pressure equivalent with the aid of the individually calibrated model may now be calculated, for example, by means of the pulse wave transmit time and pulse amplitude that are measured on a beat-by-beat basis. The $PTT^2$ (i.e., for example, a square of the pulse wave transmit time) is mapped to the systolic blood pressure value, for example, via the pressure/compliance equivalent diagram, as is indicated, for example by [5] or reference numeral 970. Said blood pressure value (i.e., for example, the systolic blood pressure value) in turn enables, along with the pulse amplitude (or the systo-diastolic volume difference ΔV), by means of the pressure/volume equivalent diagram, calculation of the systo-diastolic pressure difference ΔP and, thus, calculation of the diastolic blood pressure value, as is indicated, for example, by [6] or reference numeral 980. In other words, a difference between the systolic blood pressure value and the diastolic blood pressure value may be referred to as a pressure amplitude, for example.

Figure 10:
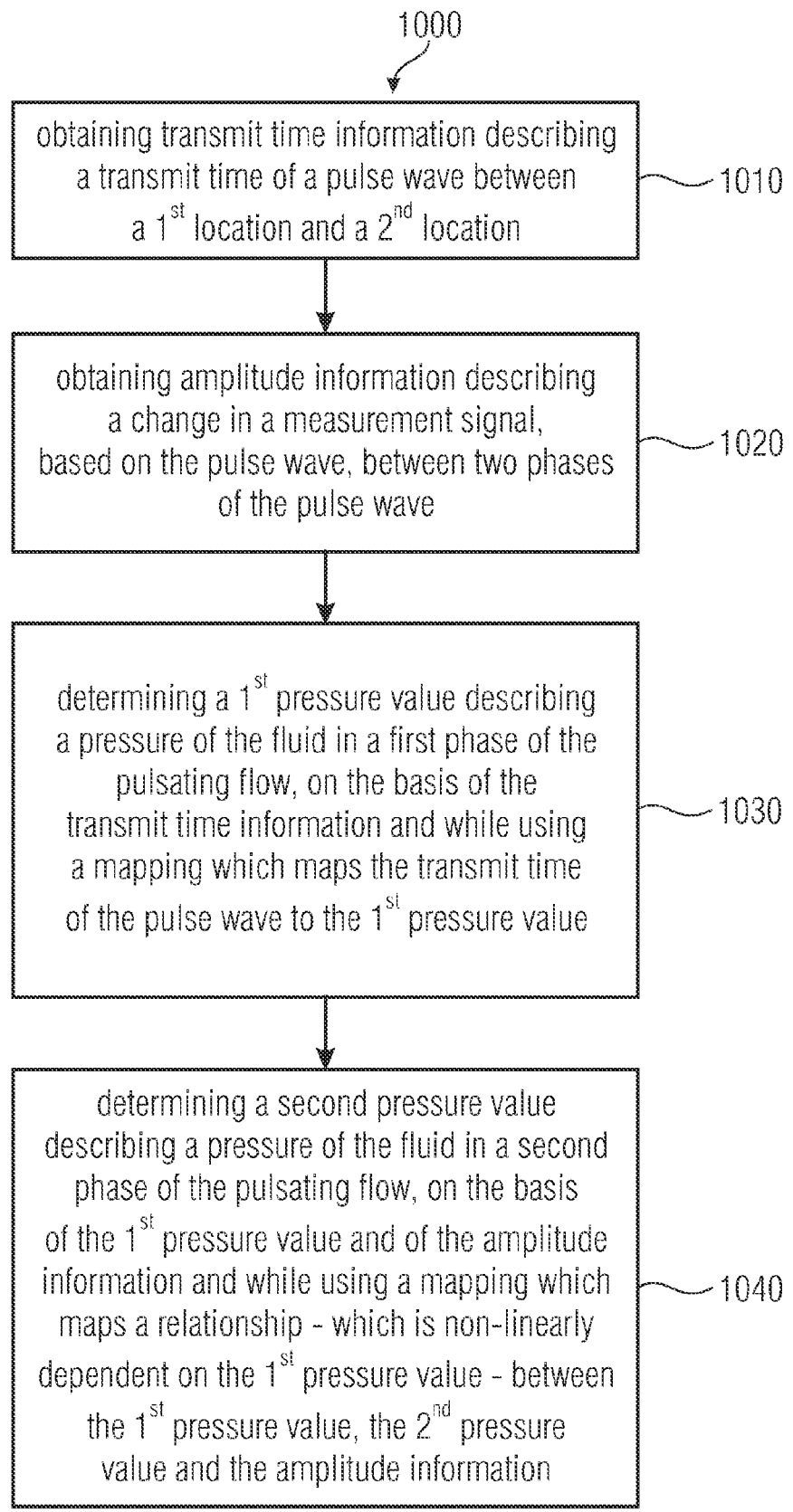
FIG. 10 shows a flow chart of a method of determining a first pressure value and a second pressure value on the basis of transmit time information and amplitude information.

FIG. 10 shows a flow chart of a method of determining two pressure values in accordance with an embodiment of the invention. The method of FIG. 10 is designated by 1000 in its entirety. The method 1000 comprises obtaining 1010 transmit time information describing a transmit time of a pulse wave between a first location and a second location. The method further comprises obtaining 1020 amplitude information describing a change in a measurement signal, based on a pulse wave, between two phases of the pulse wave. A first phase of the pulse wave may be a maximum, for example (e.g. with regard to a local pressure or with regard to a local expansion of a fluid conductor or a blood vessel), and a second phase of the pulse wave may be a stationary phase, for example, or vice-versa. The method 1000 comprises determining 1030 a first pressure value, which describes a pressure of the fluid in a first phase of the pulsating fluid, on the basis of the transmit time information and while using a first mapping, which maps a transmit time of the pulse wave to the first pressure value. The method 1000 comprises determining 1040 a second pressure value, which describes a pressure of the fluid in a second phase of the pulsating flow, on the basis of the first pressure value and of the amplitude information, while using a second mapping, which describes a relationship—which is non-linearly dependent on the first pressure value—between the first pressure value, the second pressure value and the amplitude information.

Figure 11:
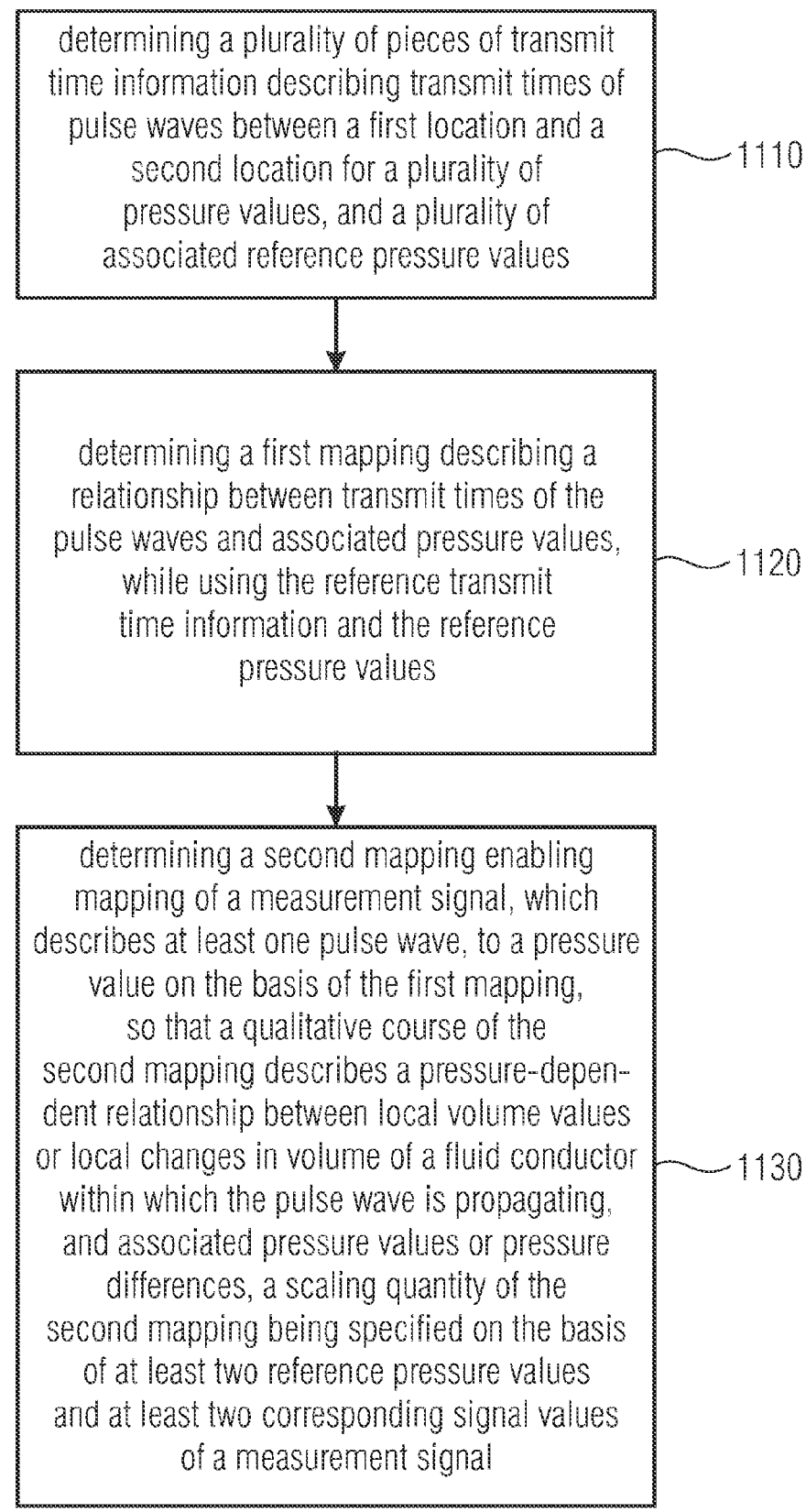
FIG. 11 shows a flow chart of a method of calibrating a pressure gauge, in accordance with an embodiment of the invention.

FIG. 11 shows a flow chart of a method of calibrating a pressure gauge in accordance with the embodiment of the invention. The method of FIG. 11 is designated by 1100 in its entirety.

The method 1100 comprises determining 1110 a plurality of pieces of reference transmit time information describing transmit times of pulse waves between a first location and a second location for a plurality of pressure values, and a plurality of associated reference pressure values. The method 1100 comprises determining 1120 a first mapping, which describes a relationship between transmit times of the pulse waves and associated pressure values, while using the reference transmit time information and the reference pressure values. In addition, the method 1100 comprises determining 1130 a second mapping, which enables mapping of amplitude information of a measurement signal describing at least one pulse wave to a pressure value, on the basis of the first mapping. The second mapping is determined such that a qualitative course of the second mapping describes a pressure-dependent relationship between local volume values or local changes in volume of a fluid conductor within which the pulse wave propagates and associated pressure values or pressure differences. The second mapping is determined such that a scaling quantity of the second mapping is specified on the basis of at least two reference pressure values and at least two corresponding signal values of a measurement signal.

In summary, it may therefore be stated that several embodiments in accordance with the invention comprise the following characteristic features:

non-invasive, continuous (beat-by-beat) estimation of an arterial blood pressure without cuff after once-only auscultatory or oscillometrical calibration of the system with regard to individual vessel physiology; and observation of a homogenous, elastic section of a vessel on the basis of the two plethysmographs on the forearm (as shown in FIG. 3, for example) and, thus, exclusion of an electromechanical latency period of the heart and of the active influences of the vascular muscles (e.g. of the arterioles) on peripheral blood-flow regulation.

It may be stated in summary that some of the embodiments described herein, or some embodiments of the system described herein, serve to perform non-invasive, continuous and no-load (without a cuff) blood pressure estimation on the basis of the pulse wave transmit time and the pulse wave amplitude. Said parameters (i.e., for example, the pulse wave transmit time and the pulse wave amplitude) are measured, e.g., by means of two plethysmographs on the forearm on a vessel section that is elastic and homogenous with regard to vascular anatomy (arteria ulnaris and arteria radialis). In this manner, the electromechanical latency period of the heart and the peripheral regulation processes as sources of error are circumvented. Once-only calibration of the underlying model and a calculation, which is subsequently possible, of the blood pressure equivalent are performed while taking into account the physiological laws, such as the pressure/volume ratios, the compliance and the pulse wave velocity of the vascular section considered.

It may further be stated, in summary, that the concept and/or method described herein may be applied, for example, in the field of non-invasive, continuous blood pressure measurement, said concept and/or method exploiting fundamental principles of vascular physiology, so as to establish relationships between the systolic/diastolic blood pressure and the plethysmography-based measured quantities of pulse wave transmit time and pulse wave amplitude, and to thus estimate the arterial blood pressure.

Plethysmography generally is a non-invasive measurement method for detecting changes in volume. In this field of application, said method is applied to measure specific changes in the volume of arterial vascular sections that are due to specific pulse waves. A rough distinction may be made, for example, between volume plethysmography, photo-plethysmography, impedance plethysmography, and capacitive plethysmography.

In the following, a brief illustration shall be provided of how some embodiments constitute an improvement over conventional systems and/or methods. Previous, or conventional, methods for non-invasive estimation of the "blood pressure" parameter are mainly based on a negative correlation between the pulse wave transmit time (PTT) and the arterial blood pressure (BP), and also on the pulse wave amplitude. To detect said pulse wave parameters, a QRS complex in an electrocardiogram (EGC) is usually selected as a starting time, and a maximum in a peripheral photo-plethysmograph (e.g. on the finger or ear) is usually selected as the arrival time of the pulse wave.

An electromechanical latency period of the heart, which ranges between the maximum myocardial excitation (QRS complex) and the actual expulsion of blood from the left ventricle, has a distorting effect on the pulse wave transmit time (PTT) to be calculated, since it cannot be assumed to be constant in all patients. In addition, averaging is performed over the passive and active properties of the arterial vascular system, which are constantly changing (from being central to being peripheral), e.g. for blood-flow regulation in the periphery, which is why only vague conclusions may be drawn in terms of the central conditions with regard to pulse wave transmit time and pulse amplitude.

For calculating a blood pressure equivalent by means of the pulse wave transmit time (and pulse wave amplitude), there are already numerous linear and non-linear models, the plurality of which are justified merely empirically and do not have any physiological background. In some embodiments of the invention, a particularly precise and/or reliable determination of pressure values or blood pressure values is enabled by the above-described physiologically-based model which is reflected, for example, in the first mapping and in the second mapping.

In summary, it may be stated that various embodiments of a pressure gauge or a blood pressure gauge have been described herein. Generally, it is to be stated that embodiments that have been described in terms of blood pressure measurement may also be employed for general pressure measurement. In this sense, a blood pressure gauge may be regarded, quite generally, as a pressure gauge as well. Any values related to a blood pressure may quite generally also be regarded as values related to a pressure.

The methods described herein may be realized in various manners. In some embodiments, a computer program may be used.

In other words, the inventive devices and the inventive methods may be implemented in hardware or in software. The implementation may be performed on a digital storage medium, for example a disk, a CD, a DVD, a ROM, a PROM, an EPROM, an EEPROM, or a flash memory, which comprise electronically readable control signals that may cooperate with a programmable computer system such that the respective method is performed. Generally, the invention thus also consists in a computer program product with a program code, stored on a machine-readable carrier, for performing the inventive method when the computer program product runs on a computer. In other words, the invention may be realized as a computer program having a program code for performing the inventive method when the computer program runs on a computer.

While this invention has been described in terms of several embodiments, there are alterations, permutations, and equivalents which fall within the scope of this invention. it should also be noted that there are many alternative ways of implementing the methods and compositions of the present invention. it is therefore intended that the following appended claims be interpreted as including all such alterations, permutations and equivalents as fall within the true spirit and scope of the present invention.

The invention claimed is:

1. A pressure gauge for determining at least one pressure value describing a pressure of a fluid flowing in a pulsating manner in a phase of the pulsating flow, comprising:
a pulse wave characterizer configured to acquire transit time information describing a transit time of a pulse wave between a first location and a second location, and amplitude information describing a change in a measurement signal, which is based on the pulse wave, between two phases of the pulse wave; and
a pressure value determiner configured to acquire a first pressure value describing a pressure of the fluid in a first phase of the pulsating flow on the basis of the transit time information and while using a first mapping which maps the transit time of the pulse wave to the first pressure value, wherein
the pressure value determiner is configured to acquire a second pressure value describing a pressure of the fluid in a second phase of the pulsating flow on the basis of the first pressure value and the amplitude information while using a second mapping,
the second mapping describes a relationship, which depends on the first pressure value, between the first pressure value, the second pressure value and the amplitude information,
the second mapping further describes a relationship between an amplitude of the measurement signal and an amplitude of the pulse wave, taking into account the first pressure value,
the second mapping describes a difference between the first pressure value and the second pressure value that is dependent on the amplitude information and on the first pressure value,
the second pressure value represents a systolic pressure value, and
the pressure gauge is implemented by a hardware apparatus, a computer, or a combination of a hardware apparatus and a computer.

2. The pressure gauge as claimed in claim 1, wherein pressure gauge is a blood pressure gauge that determines the systolic blood pressure value;
wherein the pulse wave characterizer is configured to acquire the amplitude information such that the amplitude information describes the amplitude of a measurement signal based on the pulse wave;
wherein the pressure value determiner is a blood pressure value determiner that is configured to acquire, as the first pressure value, a first blood pressure value on the basis of the transit time information and while using the first mapping, which maps the transit time of the pulse wave to the first blood pressure value, and
wherein the pressure value determiner is configured to acquire, as the second pressure value, a second blood pressure value on the basis of the first blood pressure value and the amplitude information while using the second mapping; and
wherein the second mapping describes a relationship, which depends on the first blood pressure value, between the amplitude information and a pressure amplitude of the pulse wave described by the measurement signal.

3. The pressure gauge as claimed in claim 1, wherein the pulse wave characterizer is configured to receive a first plethysmograph signal and a second plethysmograph signal and to generate the transit time information on the basis of the first plethysmograph signal and the second plethysmograph signal.

4. The pressure gauge as claimed in claim 1, wherein the pulse wave characterizer is configured to create the amplitude information on the basis of a plethysmograph signal, such that the amplitude information at least approximately describes an amplitude of the plethysmograph signal.

5. The pressure gauge as claimed in claim 1, the pressure gauge comprising at least one plethysmograph configured to provide a plethysmograph signal which describes a temporal course of a blood circulation of a blood vessel or a temporal course of a change in volume of a fluid conductor.

6. The pressure gauge as claimed in claim 1, the pressure gauge comprising at least two plethysmographs, a first plethysmograph being configured to provide a first plethysmograph signal which describes a temporal course of a blood circulation of a blood vessel at a first location, and
wherein a second plethysmograph is configured to provide a second plethysmograph signal which describes a temporal course of a blood circulation of a blood vessel at a second location.

7. The pressure gauge as claimed in claim 6, wherein the first plethysmograph and the second plethysmograph are configured to be mounted on a shared vascular section which is homogenous with regard to vascular anatomy, and
to provide measurement signals which describe a propagation of a pulse wave within the vascular section.

8. The pressure gauge as claimed in claim 6, wherein the first plethysmograph and the second plethysmograph are configured to be jointly arranged, at a predefined distance, on an upper arm, a forearm, a thigh or a lower leg.

9. The pressure gauge as claimed in claim 1, wherein the pressure value determiner is configured to evaluate, when the first pressure value is determined, a first mapping specification which at least approximately describes a relationship between a blood pressure and a compliance of a blood vessel.

10. The pressure gauge as claimed in claim 9, wherein the blood pressure determiner is configured to evaluate, as the first mapping specification which at least approximately describes a relationship between a blood pressure and a compliance of a blood vessel, a Gaussian-curve type mapping specification.

11. The pressure gauge as claimed in claim 9, wherein the pressure value determiner is configured to square, when the first pressure value is determined, a transit time value described by the transit time information, so as to acquire the first blood pressure value on the basis of the squared transit time value while using the first mapping specification describing the relationship between a blood pressure value and a compliance of a blood vessel.

12. The pressure gauge as claimed in claim 1, wherein the pressure value determiner is configured to evaluate, when the second pressure value is determined, a second mapping specification describing a relationship between a pressure value or a pressure difference and a volume value or a change in the volume of an elastic fluid conductor or a blood vessel.

13. The pressure gauge as claimed in claim 12, wherein the pressure value determiner is configured to evaluate, as the second mapping specification describing a relationship between a pressure value or a pressure difference and a volume value or a change in the volume of an elastic fluid conductor or a blood vessel, a sigmoidal mapping specification.

14. The pressure gauge as claimed in claim 12, wherein the pressure value determiner is configured to use the amplitude information as a measure of a change in the volume of an elastic fluid conductor or of a blood vessel, and
to determine the second pressure value or blood pressure value while starting from the first pressure value or blood pressure value and while taking into account the change in volume described by the amplitude information and while using a mapping specification describing a non-linear relationship between pressure or blood pressure and a volume of an elastic fluid conductor or blood vessel.

15. The pressure gauge as claimed in claim 1, the pressure gauge being configured to acquire a mapping specification, which describes the second mapping, by integrating a mapping specification which describes the first mapping.

16. The pressure gauge as claimed in claim 1, wherein the pulse wave characterizer is configured to acquire the transit time information such that the transit time information describes a duration between a point of a maximum inclination of a first plethysmograph signal and a point of a maximum inclination of a second plethysmograph signal, and to determine the amplitude information such that the amplitude information describes an amplitude of one of the plethysmograph signals;
wherein the pressure value determiner is configured to acquire, as the second pressure value, the systolic blood pressure value on the basis of the transit time information and while using the first mapping; and
wherein the pressure value determiner is configured to acquire, as the first pressure value, a diastolic blood pressure value.

17. The pressure gauge as claimed in claim 1, the pressure gauge being configured to calibrate the first mapping and the second mapping on the basis of a plurality of mutually associated pieces of reference transit time information, reference amplitude information and reference pressure values.

18. The pressure gauge as claimed in claim 1, wherein the pressure gauge comprises a calibrator;
wherein the calibrator is configured to receive a plurality of pieces of reference transit time information which describe transit times of pulse waves between a first location and a second location for a plurality of pressure values, and a plurality of reference pressure values associated with the reference transit time information,
to specify the first mapping while using the reference transit time information and the reference pressure values,
to specify a qualitative course of the second mapping on the basis of the first mapping.

19. The pressure gauge as claimed in claim 18, wherein the calibrator is configured to determine the qualitative course of the second mapping by integrating the first mapping with regard to the pressure value.

20. The pressure gauge as claimed in claim 18, wherein the calibrator is configured to specify a scaling of the second mapping on the basis of information about a difference between two pressure values which describe different phases of the pulsating flow, and on the basis of associated amplitude information describing a change in the measurement signal between the two different phases of the pulsating flow.

21. The pressure gauge as claimed in claim 1, the pressure gauge being configured
to determine or approximate, during a calibration, on the basis of reference pressure values describing a systolic blood pressure and on the basis of associated reference transit time values, a Gaussian pressure/compliance curve which describes a vascular section,
to acquire a sigmoidal pressure/volume curve by integrating the pressure/compliance curve, and
to determine a ratio between amplitude information belonging to the reference blood pressure values and a volume difference as is described by the pressure/volume curve and which corresponds to the amplitude information, as a scaling quantity while using a difference between a systolic reference blood pressure value and an associated diastolic reference blood pressure value.

22. The pressure gauge as claimed in claim 21, the pressure gauge being adapted
to square, during blood pressure measurement, transit time information that is based on a measurement,
to map the result of the squaring to the systolic blood pressure value while using the pressure/compliance curve, and
to acquire a diastolic blood pressure value while using the systolic blood pressure value, the amplitude information and the pressure/volume curve.

23. A method of determining, while using a pressure gauge, pressure values which describe a pressure of a fluid that is flowing in a pulsating manner in at least two phases of the pulsating flow, comprising:
acquiring, by a pulse wave characterizer, transit time information describing a transit time of a pulse wave between a first location and a second location;
acquiring, by the pulse wave characterizer, amplitude information describing a change in a measurement signal, based on the pulse wave, between two phases of the pulse wave;
determining, by a pressure value determiner, a first pressure value, which describes a pressure of the fluid in a first phase of the pulsating fluid, on the basis of the transit time information and while using a first mapping, which maps a transit time of the pulse wave to the first pressure value; and
determining, by the pressure value determiner, a second pressure value, which describes a pressure of the fluid in a second phase of the pulsating flow, on the basis of the first pressure value and of the amplitude information, while using a second mapping, which describes a relationship —which is dependent on the first pressure value —between the first pressure value, the second pressure value and the amplitude information, wherein
the second mapping further describes a relationship between an amplitude of the measurement signal and an amplitude of the pulse wave, taking into account the first pressure value,
the second mapping describes a difference between the first pressure value and the second pressure value that is dependent on the amplitude information and on the first pressure value,
the second pressure value represents a systolic pressure value, and
the method is performed by a hardware apparatus, a computer, or a combination of a hardware apparatus and a computer.

24. The method as claimed in claim 23, wherein the second mapping describes a relationship, which is non-linearly dependent on the first pressure value, between the first pressure value, the second pressure value and the amplitude information.

25. A method of calibrating a pressure gauge configured to determine, while using a first mapping and a second mapping, at least one pressure value which describes a pressure of a fluid flowing in a pulsating manner in a phase of the pulsating flow, comprising:
determining, by a pulse wave characterizer, a plurality of pieces of reference transit time information describing transit times of pulse waves between a first location and a second location for a plurality of pressure values, and a plurality of associated reference pressure values;

determining, by a pressure value determiner, the first mapping, which describes a relationship between transit times of the pulse waves and associated pressure values, while using the reference transit time information and the reference pressure values; and determining, by a pressure value determiner, the second mapping, which describes a relationship, that is dependent on a first pressure value, between the first pressure value, a second pressure value and amplitude information, wherein a qualitative course of the second mapping is specified on the basis of the first mapping, the amplitude information describes a change of a measurement signal from a sensor between phases of the pulse waves, the second mapping describes a difference between the first pressure value and the second pressure value that is dependent on the amplitude information and on the first pressure value, the second pressure value represents a systolic pressure value, and the method is performed by a hardware apparatus, a computer, or a combination of a hardware apparatus and a computer.

26. The method as claimed in claim 25, wherein the qualitative course of the second mapping is specified by integrating a course of the first mapping.

27. The method as claimed in claim 25, wherein a mapping parameter describing the second mapping is equal to a mapping parameter (b) describing the first mapping, or wherein a mapping parameter describing the second mapping is derived from a mapping parameter (b) describing the first mapping.

28. The method as claimed in claim 27, wherein the mapping parameter describes a pressure scaling.

29. The method as claimed in claim 25, wherein the second mapping is determined such that a qualitative course of the second mapping describes a pressure-dependent relationship between local volume values or local volume changes of a fluid conductor within which the pulse wave propagates and associated pressure values or pressure differences.

30. The method as claimed in claim 25, wherein the second mapping is determined such that the second mapping describes a relationship between two pressure values belonging to a pulse wave and an amplitude of a measurement signal created by the pulse wave.

31. The method as claimed in claim 25, wherein a scaling quantity of the second mapping is specified on the basis of at least two reference pressure values and at least two corresponding signal values of a measurement signal.

32. A non-transitory computer-readable medium including a computer program for performing, when the computer program is performed on a computer, a method of determining, while using a pressure gauge, pressure values which describe a pressure of a fluid that is flowing in a pulsating manner in at least two phases of the pulsating flow, the method comprising:

acquiring transit time information describing a transit time of a pulse wave between a first location and a second location;

acquiring amplitude information describing a change in a measurement signal, based on the pulse wave, between two phases of the pulse wave;

determining a first pressure value, which describes a pressure of the fluid in a first phase of the pulsating fluid, on the basis of the transit time information and while using a first mapping, which maps a transit time of the pulse wave to the first pressure value; and determining a second pressure value, which describes a pressure of the fluid in a second phase of the pulsating flow, on the basis of the first pressure value and of the amplitude information, while using a second mapping, which describes a relationship —which is dependent on the first pressure value —between the first pressure value, the second pressure value and the amplitude information, wherein the second mapping describes a relationship between an amplitude of the measurement signal and an amplitude of the pulse wave, taking into account the first pressure valve, the second mapping describes a difference between the first pressure value and the second pressure value that is dependent on the amplitude information and on the first pressure value, and the second pressure value represents a systolic pressure value.

33. A non-transitory computer-readable medium including a computer program for performing, when the computer program is performed on a computer, a method of calibrating a pressure gauge configured to determine, while using a first mapping and a second mapping, at least one pressure value which describes a pressure of a fluid flowing in a pulsating manner in a phase of the pulsating flow, the method comprising:

determining a plurality of pieces of reference transit time information describing transit times of pulse waves between a first location and a second location for a plurality of pressure values, and a plurality of associated reference pressure values;

determining the first mapping, which describes a relationship between transit times of the pulse waves and associated pressure values, while using the reference transit time information and the reference pressure values; and determining the second mapping, which describes a relationship, that is dependent on a first pressure value, between the first pressure value, a second pressure value and amplitude information, a qualitative course of the second mapping is specified on the basis of the first mapping, the amplitude information describes a change of a measurement signal from a sensor between phases of the pulse waves, the second mapping describes a difference between the first pressure value and the second pressure value that is dependent on the amplitude information and on the first pressure value, and the second pressure value represents a systolic pressure value.

* * * * *